United States Patent
Ritter et al.

(10) Patent No.: US 6,702,804 B1
(45) Date of Patent: Mar. 9, 2004

(54) METHOD FOR SAFELY AND EFFICIENTLY NAVIGATING MAGNETIC DEVICES IN THE BODY

(75) Inventors: Rogers C. Ritter, Charlottesville, VA (US); Bevil J. Hogg, Town & Country, MO (US); Peter R. Werp, St. Louis, MO (US); Walter M. Blume, Webster Groves, MO (US); Francis M. Creighton, IV, St. Louis, MO (US); Roger N. Hastings, Maple Grove, MN (US)

(73) Assignee: Stereotaxis, Inc., St. Louis, MO (US)

( * ) Notice: Subject to any disclaimer, the term of this patent is extended or adjusted under 35 U.S.C. 154(b) by 404 days.

(21) Appl. No.: 09/678,640

(22) Filed: Oct. 3, 2000

Related U.S. Application Data
(60) Provisional application No. 60/157,619, filed on Oct. 4, 1999.

(51) Int. Cl.[7] ............................................... A61B 17/00
(52) U.S. Cl. ......................................................... 606/1
(58) Field of Search .............................. 600/1, 4, 7, 10, 600/13, 14, 15, 16, 17, 18, 19; 33/262, 285, 263, 334; 128/899, 898; 385/285; 324/318

(56) References Cited

U.S. PATENT DOCUMENTS

| | | | | |
|---|---|---|---|---|
| 4,608,992 A | * | 9/1986 | Hakim et al. | 600/431 |
| 4,671,287 A | * | 6/1987 | Fiddian-Green | 600/363 |
| 5,049,151 A | * | 9/1991 | Durham et al. | 606/98 |
| 5,380,268 A | * | 1/1995 | Wheeler | 600/30 |
| 5,693,091 A | * | 12/1997 | Larson et al. | 623/3.27 |
| 5,980,246 A | * | 11/1999 | Ramsay et al. | 433/5 |
| 6,292,678 B1 | * | 9/2001 | Hall et al. | 600/374 |
| 6,401,723 B1 | * | 6/2002 | Garibaldi et al. | 128/899 |
| 6,530,947 B1 | * | 3/2003 | Euteneuer et al. | 623/1.11 |

* cited by examiner

Primary Examiner—Daniel Robinson
(74) Attorney, Agent, or Firm—Harness, Dickey & Pierce, P.L.C.

(57) ABSTRACT

A method of turning a medical device, having a magnetically responsive element associated with its distal end, at an operating point within an operating region inside a patient's body from an initial direction to a desired final direction, through the movement of at least one external source magnet. The at least one external source magnet is moved in such a way as to change the direction of the distal end of the magnetic medical device from the initial direction to the desired final direction without substantial deviation from the plane containing the initial direction and the desired final direction.

16 Claims, 19 Drawing Sheets

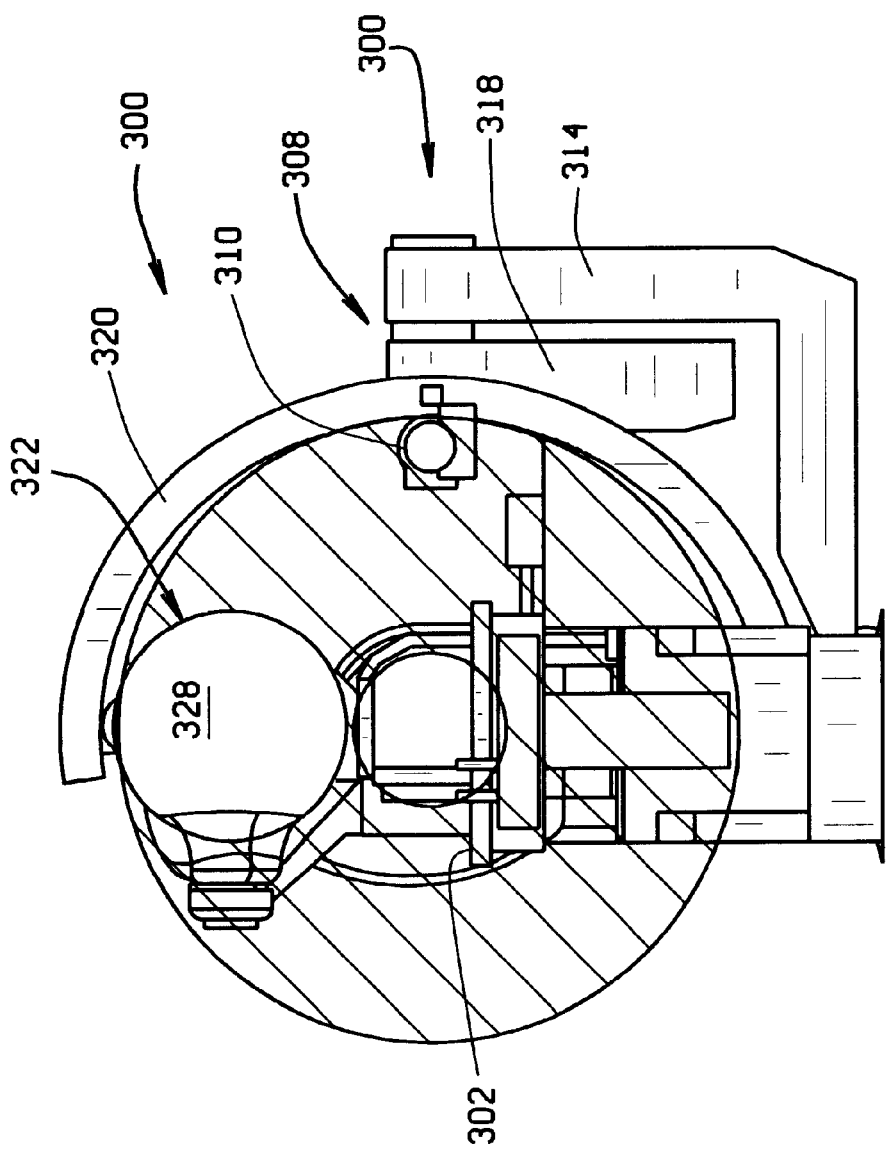

METHOD FOR SAFELY AND EFFICIENTLY NAVIGATING MAGNETIC DEVICES IN THE BODY

This application claims priority of Provisional application No. 60/157,619 filed Oct. 4, 1999.

FIELD OF THE INVENTION

This invention relates to a method for navigating magnetic devices in the body, and in particular to a method for safely and efficiently navigating magnetic devices in the body using a moveable source magnet outside the body.

BACKGROUND OF THE INVENTION

The navigation of magnetic medical devices, such as magnet-tipped guide wires, catheters, endoscopes, or other instruments, with a movable source magnet presents several difficulties in ensuring that the movement of the medical device is as the physician expects and intends. The difficulties arise for several reasons, including the lag between the direction of the magnetic field applied by the magnet and the actual direction of the tip of the medical device, and "coning" of the tip of the medical device as it deviates from the intended plane of the turn as it turns.

SUMMARY OF THE INVENTION

According to one aspect of the invention, navigation of a magnet-tipped medical device takes into account the lag between the direction of the magnetic field applied by the source magnet and actual direction of the magnet tip. It is known that the magnet tip will lag the exact direction of the magnetic field at its location by some finite amount. This lag is the result of a restoring torque due to the stiffness of the attached device (e.g., the guidewire, catheter, endoscope, or other device to which the magnetic element is associated).

This creates an ambiguity between the applied magnetic field and the actual direction of the magnet tipped device that can interfere with safe and efficient navigation. The way this turn angle ambiguity is removed is to provide a lead angle for the magnetic field which accounts for the restoring, or turn-resisting, torque of the attached medical device. According to one embodiment of this invention, information about the restoring stiffness of the medical device to which the magnet is attached (e.g., a guidewire, catheter, endoscope or other device) is included in a computer program controlling the navigation. Information of about the desired angle of turn and the desired radius (sharpness) of the desired turn can reside either in a lookup table or equation programmed in the computer. This information depends upon the properties of the device with which the magnet tip is associated, and thus will be different for each different medical device. Given the magnitude of the moment of the tip magnet and this restoring torque, which is set equal to Γ, the value of B needed to achieve the required angle θ will follow.

According to a second aspect of this invention, it is desirable to make turns in such a way as to maintain the magnet tip of the medical device in the same plane as the initial direction and the desired final direction, avoiding the problem of "coning" in which the magnet tip swings out of the plane of the turn. This is particularly important when the navigation is through the parenchyma, although even when navigating through body lumens, such as blood vessels, maintaining planarity during the turn can be important. While the movement of the source magnet usually accurately aligns the tip of the medical device in the desired final direction, the movement of the magnet does not necessarily move the tip in the desired plane.

BRIEF DESCRIPTION OF THE DRAWINGS

FIG. 7I is an end elevation view of the single magnet system showing the work envelope in which the source magnet can move in an annulus around a patient's head and showing the clearance between the work envelope of the magnet and the imaging system;

Corresponding reference numerals indicate corresponding parts throughout the several views of the drawings.

DETAILED DESCRIPTION OF THE PREFERRED EMBODIMENT

Figure 1:
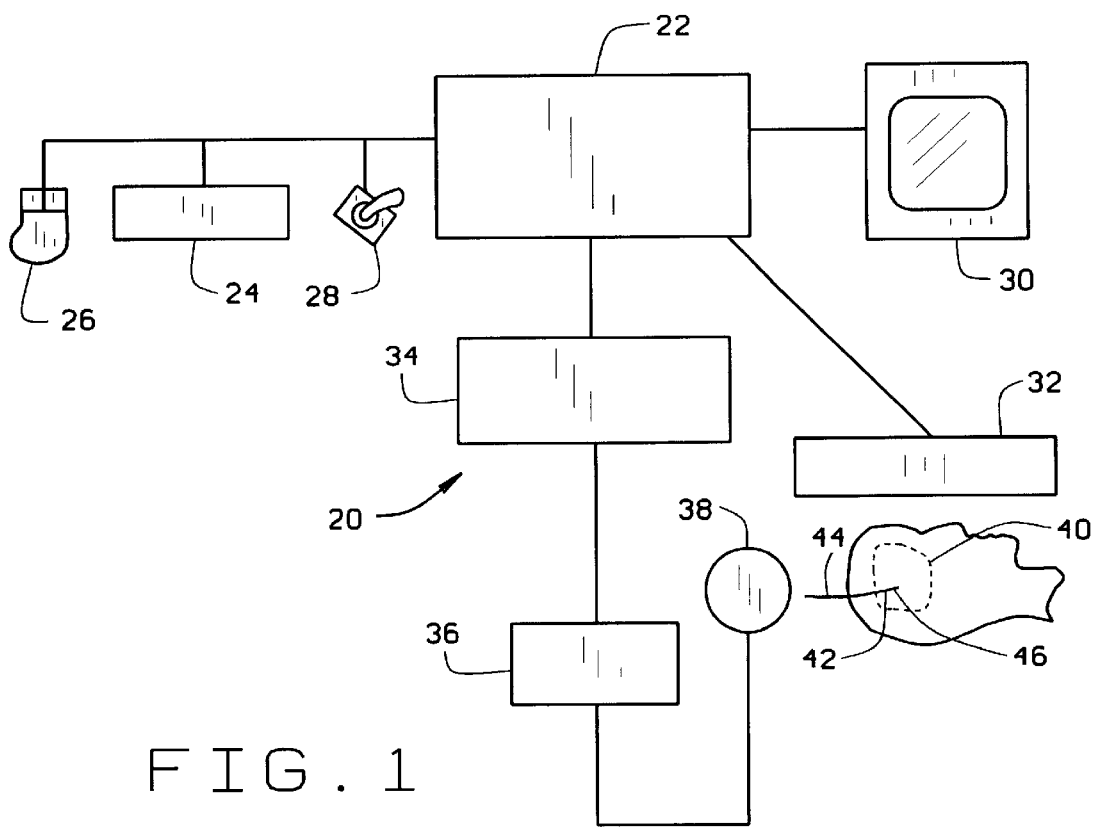
FIG. 1 is a schematic diagram of a system for safely and efficiently navigating in accordance with this invention.
Figure 2:
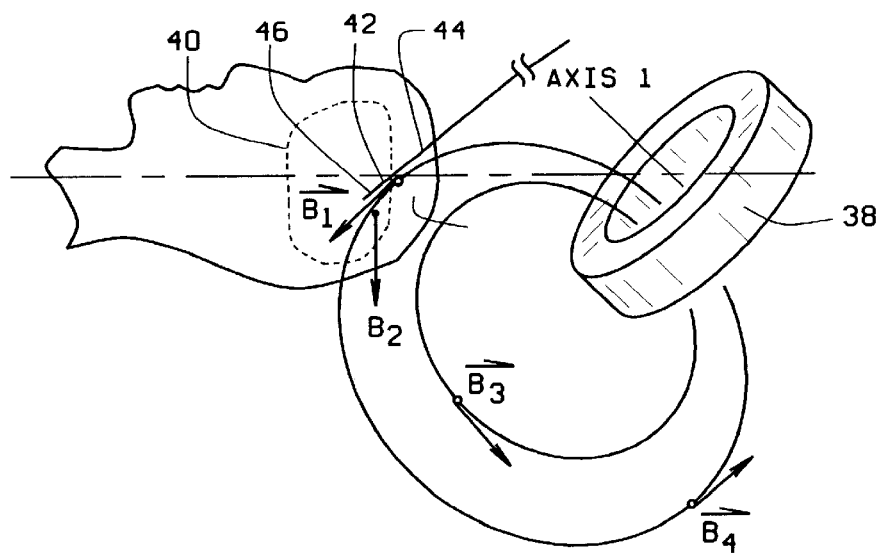
FIG. 2 is an enlarged schematic diagram of the source magnet and patient.

In accordance with this invention, a magnetic medical device is safely and efficiently navigated in the body using an externally applied magnetic field. The navigation system 20 for implementing the methods of this invention is shown schematically in FIG. 1 as comprising a computer 22 having a keyboard 24, mouse 26 and joystick 28 for inputting the physician's instructions. Of course not all of these input devices are necessary, and other input devices can be used as well. A display 30 is also connected to computer 22 to allow the physician to operate the system and monitor the navigation. Imaging apparatus 32 is connected to the computer, which processes the signals and displays images of the operating region on the display 30. A controller 34 is connected to the computer for controlling an articulation mechanism 36 that moves the source magnet 38. The magnet 38 in turn creates a magnetic field in the operating region 40 of the patient, and more particularly at the operating point 42 in the operating region, to control the orientation of a magnetic medical device 44 having a magnet tip 46.

The magnetic medical device 44 may be any medical device that the physician wants to navigate in the body, for example a guide wire, a catheter, an endoscope, etc. The medical device 44 has a magnet tip 46 associated with it that is of sufficient size and shape to be responsive to an applied magnetic field and/or gradient from the external source magnet 38 for navigating the medical device. The magnet tip 46 may be a permanent magnet or a permeable magnet. In this description, it is assumed that the magnet tip 46 is a permanent magnet, with the magnet field aligned along the longitudinal axis of the magnet. One of ordinary skill in the art could readily adapt this invention for use with permanent magnets of other configurations, or for use with permeable magnets.

In general, the magnetic medical device 44 is located at a particular operating point 42 within a larger operating region 40 in the patient. The operating region 40 is the region within the patient that the external source magnet 38 can apply a sufficient magnetic field to affect the direction of the magnetic medical device 44.

The source magnet 38 may be a permanent magnet, but it is preferably an electromagnet, and more preferably a superconducting electromagnet. The source magnet 38 may actually comprise more than one magnet. The source magnet 38 is mounted on an articulation device 36 that can move the magnet 38. The articulation device 36 can translate and/or rotate the source magnet. In the simplest case the articulation device might permit two rotations of the source magnet, or perhaps two rotations of the magnet combined with a single translation, for example toward and away from the patient. In the most elaborate case, the articulation device might permit two rotations of the source magnet, and three translations of the source magnet in three mutually perpendicular directions.

The imaging apparatus 32, may be, for example, bi-planar fluoroscopy equipment for imaging the operating region 40. Bi-planar fluoroscopy allows the location and sometimes the location and the direction of the magnetic medical device 44 (or at least the distal end of the magnetic medical device) to be determined.

The invention relates to making a safe and proper turn efficiently. A proper turn is defined as one in which the distal end of the magnetic medical device 44 remains in the plane containing the initial direction of the magnetic medical device and the desired final direction of the magnetic medical device. It is desirable to move the source magnet 38 in such away as to effect the turning of the magnetic medical device 44 in a plane. There are typically a number of movements of source magnet 38 that can turn the magnetic medical device 44 from a given initial direction to the desired final direction. However, some of these possible movements will cause the magnetic medical device 44 to sweep out of the plane of the proper turn, in a motion known as "coning" that can unnecessarily disturb surrounding tissue. Others of these possible movements will be inefficient because of the significant movement required of the source magnet 38. Still others of these possible movements will be prohibited by practical considerations, such as limitations on the rotation or translation of the magnet, interference with the equipment surrounding the magnet and the patient, imaging equipment, and imaging beams. It is important to select a magnet motion that is both safe, i.e. causes a "proper" turn, and efficient, i.e. one that is not unnecessarily of high complexity and long duration.

Lag from the Applied Magnetic Field

According to a first aspect of this invention, safe and efficient navigation is achieved by taking into account the lag between the actual orientation of the medical device 44 and the orientation of the magnetic field applied by the source magnet 38. The magnetic torque vector is conventionally identified as $\Gamma$, and is given by the formula:

$$\Gamma = m \times B \qquad (1)$$

when m is the magnetic moment (a vector) of the magnet tip 46. The magnitude of this torque is $\Gamma = mB \sin\theta$, where m is the magnitude of m, B the magnitude of B, and $\theta$ the angle between the vectors m and B. For a permanent magnet tip 46, with magnetization aligned in the usual way along its longitudinal axis, there is zero magnetic torque when the magnet tip is aligned exactly along B, and a maximum torque when the magnet tip 46 is perpendicular to (90 degrees away from) B.

Depending upon the size of a turn (or the radius of curvature at a point in a continuous path) and the stiffness of the attached device, a lead torque is needed to cause the magnet tip to turn in the correct direction. Too much lead torque will turn the magnet tip too far, and too little lead torque will not adequately orient the magnet tip in the proper direction.

Where the magnet tip 46 is a permanent magnet, the moment m is fixed geometrically, but where the magnet tip is a permeable magnet, the moment m will rotate to an intermediate direction between the field direction and the longitudinal axis of the magnet tip. Therefore, equation (1) will apply exactly to the moment, but only inexactly to a fixed geometrical aspect, say the axis, of an elongated permeable magnetic tip. This is because m shifts with B in a permeable magnet. In the remainder of this description, it will be assumed that the magnet tip 46 is a permanent magnet magnetized along its longitudinal axis, unless otherwise specified. A person of ordinary skill in the art could readily calculate characteristics of a permeable tip moment, and use them in a similar fashion.

In making a turn, whether manually or automatically with the aid of a computer, the need for a lead torque must be anticipated. In one embodiment of the present invention, information about the restoring stiffness of the medical device 44 to which the magnet tip 46 is attached (guidewire, catheter, endoscope, electrode, or other device) is included in the program controlling the navigation. Information about the desired angle of turn and the desired radius (sharpness) of the desired turn can reside either in a lookup table or equation programmed in the computer 22. This information depends upon the properties of the medical device 44 with which the magnet tip 46 is associated, and thus will be different for each different medical device. Given the magnitude of the moment of the magnet tip 46 and this restoring torque, which is set equal to Γ, the value of B needed to achieve the required angle θ will follow.

The desired angle of turn can be input, for example, using two point or three point navigation methods such as those disclosed in co-pending U.S. patent application Ser. No. 09/020,798, filed Feb. 9, 1998 entitled "Device and Method for Specifying Magnetic Field for Surgical Applications", incorporated herein by reference, or co-pending U.S. patent application Ser. No. 09/370,067 filed Aug. 6, 1999, entitled "Method and Apparatus for Controlling Catheters in body Lumens and Cavities", incorporated herein by reference.

Making A Proper Turn

According to a second aspect of this invention, safe and efficient navigation is achieved by taking into account possible deviations of the magnet tip 46 of a medical device 44 between the initial direction and the desired final direction caused by the movement of the source magnet 38. Generally, the source magnet(s) 38 employed in magnetic navigation are designed so as to have fields which can be represented unambiguously. Moreover the articulation mechanism 36 for moving the source magnets 38 is designed to maneuver a source magnet to a position and orientation needed to apply the required field and/or gradient at the operating point 42 where the magnet tip 46 is located. The sometimes complex field shape of source magnet 38 generally demands a complex approach to moving the source magnet to turn magnet tip 46, including translation and/or rotation of the source magnet. However, known symmetries of the source magnet 38 can reduce its complexity, cost, and weight of the articulation mechanism. For example, the field of a common solenoid coil has complete symmetry about its longitudinal axis, and thus rotation about the longitudinal axis does not change the field at the operating point in the patient. However, rotations about two mutually perpendicular axes that are perpendicular to the longitudinal axis can provide any change needed in the orientation of the magnetic field at the operating point. In general these two rotations, combined with one or more simple translations for locational purposes, can provide several alternate ways of changing the magnetic field vector at the operating point. While these alternatives provide articulation flexibility, they also make calculation of specific navigation paths difficult.

It is convenient to focus on a coordinate system fixed in the frame of reference of the source magnet 38, and view the (ultimately moving) position and orientation of the magnet tip 46 in the patient as it moves in this frame when the magnet is rotated. The essence of the desired turn will be to move the source magnet 38 in the patient frame of reference in a manner such that the magnetic field changes direction smoothly and in the plane formed by the initial direction and the desired final direction, i.e., the "proper turn" described above.

A first step in calculating a safe, efficient turn is the definition of the plane in which the magnet tip remains during the turn. This plane can be specified as a unit vector n perpendicular to it and determined from the equation $$n = (V_1 \times V_2)/|(V_1 \times V_2)| \quad (2)$$

i.e., a unit vector along the direction of the cross product of $V_1$ and $V_2$, where $V_1$ represents the initial direction and $V_2$ represents the desired final direction.

The proper movement of the source magnet 38 may involve translations and/or rotations. The method incorporating "Euler angles" is a convenient and well-known tool for treating the rotations of an object such as the source magnet. Goldstein, "Classical Mechanics" (Second Edition), Addison-Wesley Publishing Co. (1980), incorporated herein by reference, describes matrix operations for keeping track of vectors in such rotations. It is significant that these rotations are "noncommutative", meaning that sequential rotations lead to a final direction which depends on the order of the individual component rotations, i.e., the order of the rotations is important. This noncommutative nature of rotational operations in mechanics must be taken into account when implementing rotations.

In the case of the static magnetic fields created by the source magnets 38 preferably employed in this invention, the simplest possible rotation which will provide a proper turn is chosen. Even so, such a turn, made with the simplest source magnet rotation and translation, but without full regard for the magnetic field shape, could result in a magnetic field vector progression at the operating point 42 at the magnet tip 46 which would lead to a turn with undesirable and possibly dangerous intermediate directions.

Figure 3:
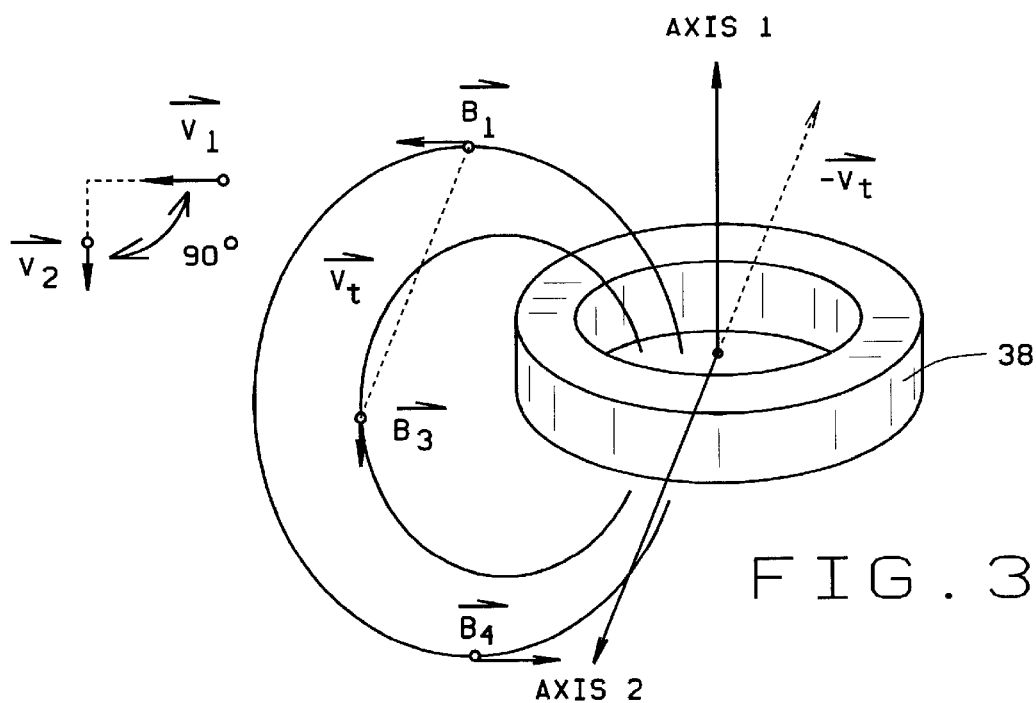
FIG. 3 is a schematic view of the source magnet, showing some of the field lines.

In FIG. 3, a source magnet 38, in the form of a simple coil, is shown with a few of its field lines, which are symmetrical about its longitudinal axis (Axis 1). The initial position and orientation of tip magnet 46 is represented by vector $V_1$, and the desired final position and orientation of the tip magnet after a 90 degree turn is represented by vector $V_2$ after the turn. Each point on each field line of source magnet 38 is a magnetic field vector B, and each field line is in a plane that that contains the coil axis (Axis 1) and is referred to as an "axial plane."

Once the direction or directions of the required magnetic field(s) are known for a desired turn, a movement to cause the source magnet 38 to apply the required field at the operating point 42 is determined. For simplicity in describing this second aspect of the invention, it will be assumed that the magnet tip 46 will orient itself exactly along a field line at its location. This implies that the initial position before a turn, and the desired final position after a turn, lie along a field line of the source magnet 38. This assumption that V lies along B is important where, for example, the imaging system used to monitor the procedure can only locate the position of the magnet tip 46, and not its orientation. For simplicity in describing this second aspect of the invention, it is also assumed that the magnet tip 46 is small enough to be represented approximately by a vector at a point.

Figure 3A:
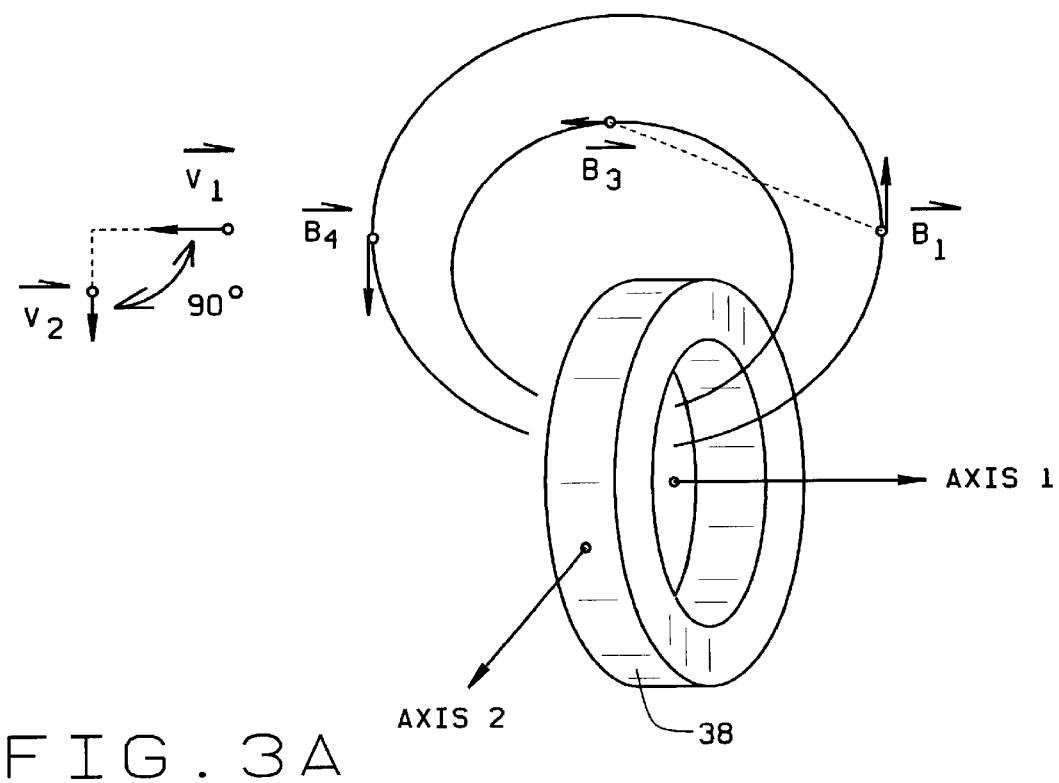
FIG. 3A is a schematic view of the source magnet shown in FIG. 3 after a rotation about Axis 2.

To illustrate the generally multiple sets of magnet motions that can accomplish a given turn in a patient, FIGS. 3 and 3A show two alternate ways to rotate a field vector parallel to $V_1$ in a patient to a new direction parallel to $V_2$ at essentially the same point in the patient. In FIG. 3 a translation of $-V_t$ upward in the figure of the source magnet 38 to relocate the operating point from $B_1$ to point $B_3$ will accomplish this 90 degree turn of the field at a given point in the patient.

In FIG. 3A the source magnet 38 is shown rotated clockwise 90 degrees about Axis 2, which brings field point $B_4$ into a position parallel to the desired direction $V_2$. It may or may not be necessary to translate the source magnet 38 to bring the new location of $B_4$ to the starting position of $B_1$, i.e., to the turning point in the patient.

The rotation and translation of the source magnet 38 preferably occur simultaneously, retaining the proper relationship between translational speed and rotational angular velocity, so as to maintain the field direction (with the magnet tip 46 crossing from field line to field line of the source magnet 38 as necessary while the source magnet rotates and translates) so that the directional change of the field lines crossing the region between point $V_1$ and point $V_2$ smoothly turn the magnet 46 as the medical device 44 progressed in feeding the magnet tip forward through the turn. If the turn is very sharp, the vectors would remain nearly at a point, and only change direction.

Depending on the capabilities of the articulation device for the source magnet 38, one of the many possible movements (translation and/or rotation) of the magnet may be more efficient than the others. For simpler, less expensive articulation mechanisms, not all of the possible movements may be available. The selected movement can not always be the most efficient turn, and structural limitations of the magnet such as placement of the cryocooler, power connections, etc., will sometimes prevent the use of the most efficient turn. In such cases a proper movement will not be the most efficient, but it should at least meet the requirement of maintaining the magnet tip in the plane of the turn.

Figure 4:
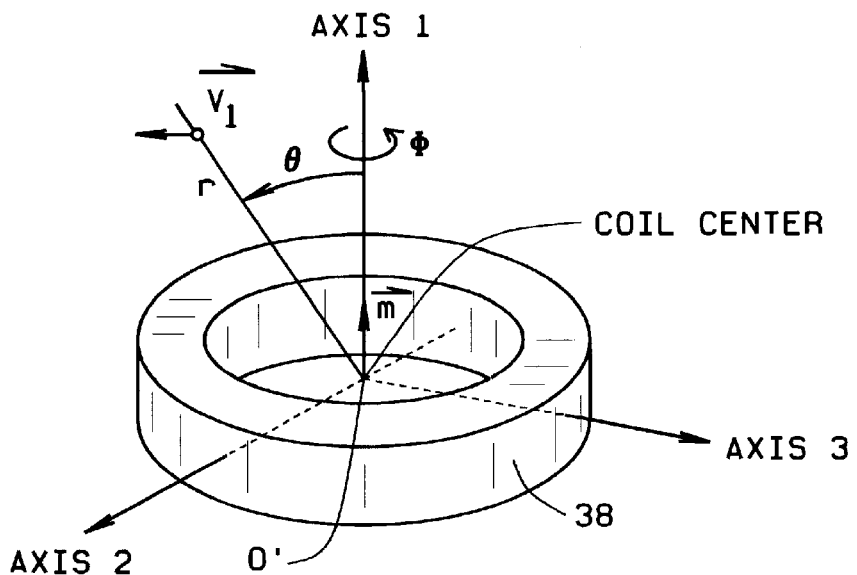
FIG. 4 is a schematic view of the source magnet with a polar coordinate system superimposed at the center of the source magnet.

As shown in FIG. 4, a spherical coordinate system is useful in describing the position of the location of $V_1$ relative to the source magnet 38. In this coordinate system, r is a vector from the center of the source magnet 38 to the operating point 42 (i.e., the location of the magnet tip 46); $\theta$ is the polar angle from the axis of the source magnet (Axis 1) down to the line r; and $\phi$ is the azimuthal angle around Axis 1 of the plane of r and Axis 1, relative to an arbitrary fixed reference plane containing the axis. Because of axial symmetry of the field of the source magnet, any motional change only in $\phi$ will result in no change in the field at $V_1$.

There are two types of planes in this coordinate system of significant usefulness in visualizing the coordinates and motions. The first type are the axial planes, which are any planes that contain both the field line and the magnet axis. The second type are planes perpendicular to the axial plane. When this second type of plane lies on the midplane of the magnet, it is referred to as the equatorial plane. Since rotation about the axis of the source magnet 38 (Axis 1) does not change the field at a point, a useful totally orthogonal system would have two other axes perpendicular to the source magnet's axis (Axis 1) and to each other. These axes are indicated as Axis 2 and Axis 3 in FIG. 4, and they lie in the equatorial plane of the source magnet 38. Axes 2 and 3 are shown schematically in FIG. 4, and could be physically implemented with a gimbal apparatus to allow the source magnet to rotate about these two axes. A usable articulation mechanism need only have two of these three axes, and it would still be capable of turning the coil to any orientation, albeit with reduced freedom of intermediate motion.

A second major part of a turn is the calculation of the particular magnet articulations for causing the magnetic field line(s) themselves to execute the proper turn. For this action (which would preferably be implemented with a computer program) there must either be an equation or lookup tables of the magnetic field for every possible orientation at every point in the operating region 40 in the patient. An ideal dipole, a special magnet with a simple equation for its field, illustrates this point. It will be appreciated that a more realistic equation (or a finite-element equivalent calculation) will also retain the azimuthal symmetry of this magnet). In the magnet coordinate system of FIG. 4, r=ix+jy+kz=ir sin $\theta$ cos $\phi$+jr sin $\theta$ sin $\phi$+kr cos $\theta$, the field a dipole is given by $$B=(\mu_o/4\pi)[-(m/r^3)+3(m\cdot r)r/r^5] \quad (3)$$

where m is the moment of the dipole (now representing the source magnet 38) and falls along the source magnet axis (by convention the z-axis), r is a vector between m (at the coil center) and the operating point in the patient, and r is its magnitude. As shown in FIG. 4, m is located and aligned along the z-axis in the most efficient use of that coordinate system. The dot product m·r is then mr cos $\theta$, where m is the magnitude of the magnetic moment.

With the magnet tip 46 located at r in the source magnet coordinate system and the initial vector directions and desired final vector directions of the magnet field at that position, in both the source magnet and patient coordinate systems, it is necessary during the turn to transform each incremental B in the source magnet coordinate system into B in the patient coordinate system while assuring that its direction remains in the plane of the proper turn. This can be implemented with computer 22 having the full equation or a lookup table with an efficient search engine. The computer 22 must first establish the location and orientation of the magnet tip 46 in the magnet coordinate system, i.e., $V_1$. Then it must establish $V_2$ in this coordinate system, and the plane of rotation $n_a$. This navigation will now be described in more detail.

Two prototypical cases establish that any turn where the magnet tip lies along a field line can be made through a combination of translations and rotations. In both of these cases the magnet tip starting position is along a field line, and therefore in an axial plane. In the first such case, both $V_1$ and $V_2$ are oriented in an axial plane, and in the second characteristic case $V_1$ is oriented in an axial plane and $V_2$ is perpendicular to that plane. All other possible turns where the magnet tip initially lies along a field line can be considered as some combination of these two special cases, with appropriate trigonometric projections.

First Prototypical Case

In the first case where $V_2$ lies in a plane containing the axis or the source magnet 38 (Axis 1) and $V_1$, then a rotation in that plane, which can be called the "starting plane" is necessary for a proper turn. As noted above, the vector direction of any plane is a vector of unit length which is perpendicular to the plane. Rotation in this plane is a rotation about a virtual axis perpendicular to that plane. This virtual rotation axis $n_a$ is defined by analogy to equation 2:

$$n_a=(V_1 \times V_a)/|(V_1 \times V_a)|, \quad (4)$$

where $V_a$ is a vector along the axis of the source magnet 38. This plane is chosen for convenience because it contains $V_1$, and it is magnetically the same as any other plane containing the axis of the source magnet 38. Therefore a vector $V_1$ located in a plane at any azimuthal angle $\phi$ will satisfy equation (4) for this case. However, only rarely will $n_a$ happen to be parallel to Axis 2 or Axis 3 of FIG. 4. Instead, the most general rotation can be formed from a trigonometric combination of rotations about these two axes. For example, if the axis $n_a$ were found in one case to be 45 degrees clockwise (looking down on the coil) from Axis 2, it would mean that the front of the coil between Axis 2 and Axis 3 would tilt up to perform a clockwise rotation about the $n_a$ axis. Looking toward these axes, Axis 2 would rotate counterclockwise, and Axis 3 would rotate clockwise (looking along this unit vector). In this case, both axes would rotate at the same angular rates.

Figure 5:
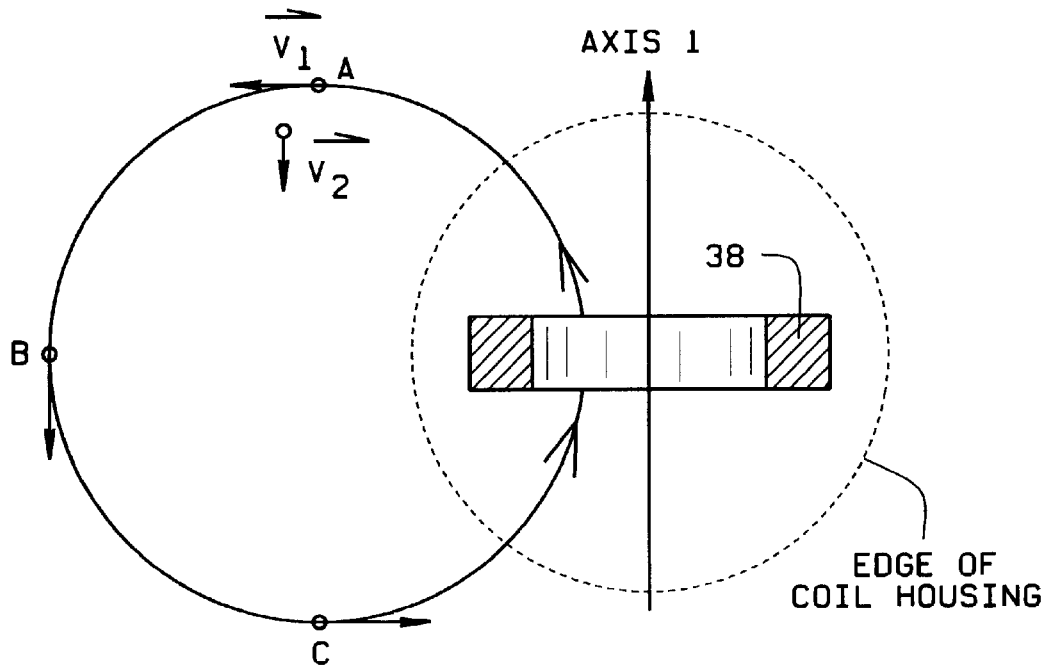
FIG. 5 is a vertical cross-sectional view of the source magnet, illustrating the magnetic field directions useful for a turn in an axial plane.

FIG. 5 illustrates this turn in an axial plane (with $V_1$ and $V_2$ separated by an exaggerated distance). The starting point is labeled A, and B and C identify two other points around that field line which passes through A. For clarity, only a single field line is shown. (The circular shape shown for the field line is not intended to be a highly accurate representation of the shape of a field line from a real coil.) The plane of turn, designated by $n_a$, is oriented out of the page.

The field line at point B is parallel to $V_2$, and a simple translation of the source magnet 38 to bring point B to the location of $V_2$ would accomplish a turn of the magnet tip 46 in the patient. However, the translation would have to be judiciously chosen on some curve in order for the field strength to remain unchanged during the turn. It is desirable that the field strength remain constant to reduce variations in the direction of the magnet tip 46. Moreover, the translational path should lie in the starting plane. With these choices, the turn would be a proper one, albeit probably not efficient. To accomplish this turn, the translational path would be determined by moving from point A to point B in the field line of equation (3) or an accurate line calculated for a real coil, and then translating the source magnet in the inverse direction of that path. To maintain the curve as a proper turn would involve a choice of fixed $\phi$. An obvious choice for an efficient (although perhaps not the most efficient) proper turn in this case would be a translation with $\phi$ and magnitude B fixed at each step of the turn and with $\theta$ changing smoothly and monotonically.

Second Prototypical Case

In the second prototypical case, $V_1$ is in an axial plane but $V_2$ is perpendicular to that plane so that rotation about a different virtual axis $n_2$ is necessary. Since $n_a$ still defines the starting plane, the vector axis of rotation, $n_2$, is perpendicular to both $V_1$ and $n_a$ $$n_2 = (V_1 \times n_a)/|(V_1 \times n_a)| \quad (5)$$

Figure 6A:
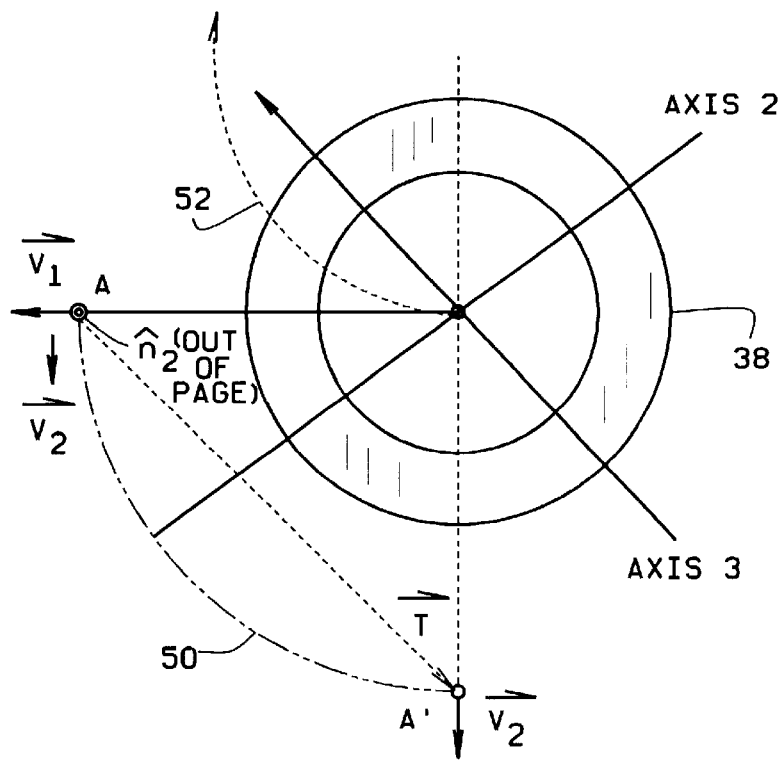
FIG. 6A is a top plan view of the source magnet, illustrating the magnetic field directions useful for a turn from an axial plane at point A in FIG. 5.
Figure 6B:
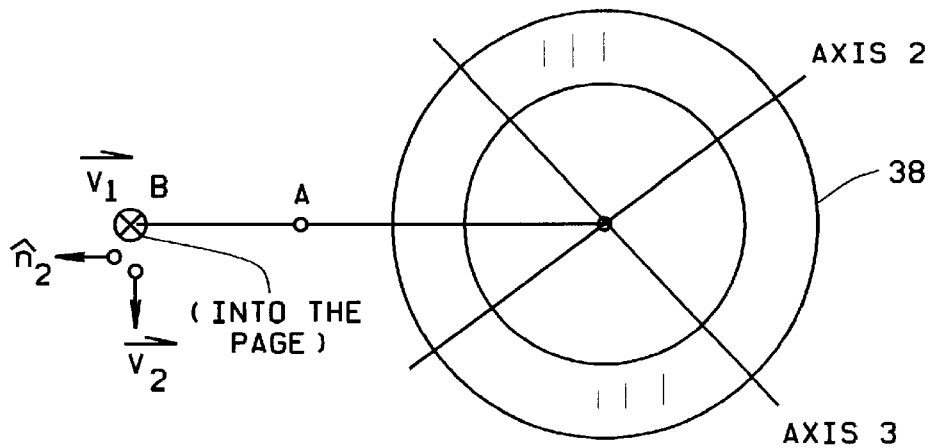
FIG. 6B is a top plan view of the source magnet, illustrating the magnetic field directions useful for a turn from an axial plane at point B in FIG. 5.

Two turns for this second general case are illustrated in FIGS. 6A and 6B, which are views looking down on the axis of the source magnet 38. A first turn of the second prototypical case is illustrated in FIG. 6A where the starting location is shown as a projection of point A of FIG. 5 onto this view. The field rotation is shown as $n_2$, out of the paper.

It is apparent that a pure rotation of the source magnet 38 about its axis, needed to accomplish $n_2$, cannot be effective for this proper turn because of field line symmetry. A translation, approximately along Axis 3 and in direction T, would bring the magnet tip 46 to point A' in the frame of reference of the source magnet 38, as shown by the straight dashed line, and would accomplish a proper turn. However, since the distance between the path and the source magnet axis varies, the field strength will vary during such a turn. Instead, a translation of the source magnet 38 in which point A progressed in a circle around the source magnet axis, would result in a proper turn with constant field magnitude. Such a path is shown as a dot-dashed line 50. (This is the trajectory of the magnet tip 46 in the frame of reference of the source magnet. The movement of the source magnet 38 in the operating room will be opposite to this motion and is show as dot-dashed line 52).

A second turn of the second prototypical case is illustrated in FIG. 6B, where $V_1$ is again in the axial plane, but now is located as point B of FIG. 5, i.e., pointing into the paper in this view. Now $n_2$ points away from the coil. This turn is the simplest, and is accomplished purely by rotating the coil about the axis from the center of the magnet out to the location of $V_1$. For generality, this is shown as different from Axis 2 or Axis 3. Such an axis is established trigonometrically in the same manner as described above. (A prior pure rotation about the coil axis could establish one of these as the turn axis without disturbing the magnet tip, but with some simpler articulation mechanisms, such a rotation might have been considered generally unnecessary and therefore not available).

Having established the qualitative nature of proper turns, we now describe quantitative means of calculating the magnet articulations needed for navigation. Navigation in the operating region of the patient would intuitively seem to be most directly visualized and calculated in the patient reference system. This would, however, entail transformation of the rotating and translating magnetic source field into that reference system, which would be difficult, given that the source magnet field often cannot be put into analytical form. (A lookup table of five dimensions could contain all transformations to follow, but is just a modification of the following method). While transforming a field from one frame of reference to another can be complex, any specific magnetic field vector is easily transformed between the coordinate systems. This method has been devised to avoid the difficulty of field transformations. It provides ways to test trial turns for proper characteristic, and to break up a full turn as necessary to maintain the turn in a sufficiently close planar form. In addition, an essential feature in this method is a means of removing the ambiguity of a turn, i.e., a method of limiting the possibilities to a small, practical "neighborhood" of trial turns, and then choosing the "best" proper turn from among the possible trial turns.

Figure 8:
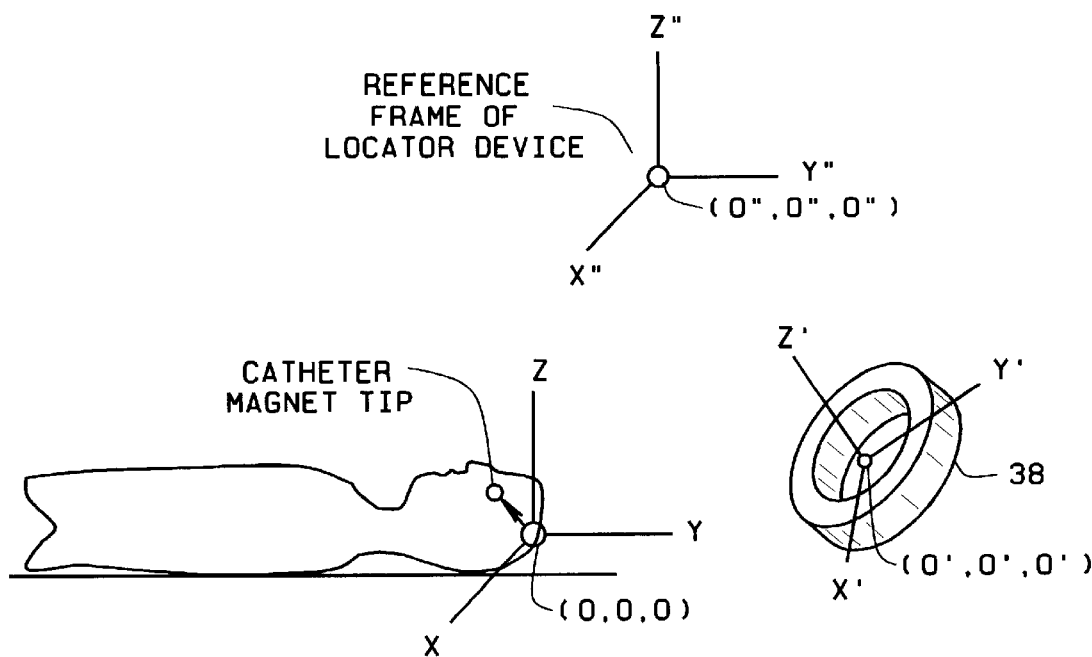
FIG. 8 is a schematic view showing the frames of reference of the source magnet, the patient, and a locator device.

The procedure works in the reference frame of the source magnet after the desired vector in the patient coordinate frame is transformed, and then calculates and transforms each necessary field vector into the patient frame. Sometimes this can be done automatically with search methods and equations. The procedure can involve steps in purely rotating a field vector through a turn from $V_1$ to $V_2$ in the patient frame, using operations in the source magnet frame, and taking care that these operations take into account when a rotation in that frame will in addition require a translation of the source magnet 38 in the patient frame. For the method to work, the relationship between the two frames must be known. An external locating means can be provided to connect the location and orientation of the frame of reference of the source magnet to the patient frame. One example of such a locating means is disclosed in Van Steenwyk et al., U.S. Pat. No. 4,173,228, issued Nov. 6, 1979, for Catheter Locating Device, incorporated herein by reference. In the following description, and as shown in FIG. 8, unprimed coordinates (x, y, z) will designate the patient frame, and primed coordinates (x', y', z') are in the source magnet frame. Third, coordinates (x", y", z") are used for the room coordinates, i.e., the coordinates in which the locator device is fixed. In one embodiment, the locator device establishes the relationship between the magnet tip on the medical device and the source magnet, as described above. In another embodiment, the locator device might establish the relationship between the source magnet and a point on a patient, fixed in the room, in which case the orientation of the magnet tip 46 would have to be determined in some other way. Bi-planar fluoroscopic imaging can locate the magnet tip 46, but does not always give good information about its orientation. Commercial magnetic field locators are available which can also find the orientation of the magnet tip 46. Other imaging systems can use combinations of imaging modalities. In the following discussion, any appropriate locating and/or imaging devices can be used.

Generally, the transformation problem has five degrees of freedom (although, depending upon the application, it is not necessary that the articulation device must have all of these degrees of freedom). The translation of a vector between two reference frames has 3 components, and the rotation of a vector has 2 components (polar and azimuthal angles). The field vectors to be transformed need not be rotated around an axis which is collinear with their own directions.

Two types of vectors have been discussed. Vectors which yield the position of an object in a reference frame, and vectors which describe a magnetic field at a point. These are treated separately and explicitly below.

The operating position location in each frame of reference can be specified as a vector relative to the origin in that frame of reference, and a positional transformation in a given frame is then a vector addition or subtraction. (There is no need to rotate the position vectors except when dealing with exclusion zones.) However, the field vectors must in general be rotated and translated. In the patient frame, the location vector is simply a vector from a fixed origin in that frame out to the operating point (where the magnet tip 46 is located). In the frame of the source magnet 38, however, the origin for the location vector will change each time the source magnet is translated, as described below. FIG. 8 shows frame axes in these frames plus the locator frame. With some location methods, the origin of the patient frame could be at the operating point 42 where the magnet tip 46 is located, and would move as that point moved. A locator system operating throughout the duration of the procedure would maintain information about the locations of (0, 0, 0) and (0', 0', 0') relative to its own fixed frame (0", 0", 0").

The location and direction of vector $V_1$ in the frame of reference of the patient is transformed into $V_1'$ in the frame of reference of the magnet source 38 by well known vector algebraic methods. In general this will require separate vector translation and rotation operations. (Translations involve vector sums or differences, rotations involve matrix multiplication.) Given $V_1$, the three coordinates of the position of the vector $V_1'$ are found by simple addition of the known coordinate origin transformation from (0, 0, 0) to (0', 0', 0'). The needed information is known, as stated above, from external locating means. Of course, if the external locating means is operating continuously, this step will be immediate and trivial. Otherwise, any magnet movement and rotation since an initial "calibrating" relative location and orientation by that locating means will necessarily have been recorded in the processor and will be accounted for. In either case, one more step is necessary. The vector $V_1'$ must be located relative to (0', 0', 0'), and its orientation must also be found. If $V_1$ is the very first vector in the procedure $V_1$, will be found in the calibration just mentioned. Otherwise, $V_1$ will be known in the processor, which must continually account for each step of a procedure, and within certain accuracy can retain a "dead reckoning" of translations and rotations of the source magnet 38, as well as translation and rotation of the magnet tip 46.

It is sometimes necessary and usually desirable in navigation for the magnetic field strength to remain constant. This provides a useful constraint on the navigation calculations. One of ordinary skill in the art would know how to change the magnetic field strength, if needed, given this method for a turn made at constant field strength. In the constant field strength method, the location of $V_1'$ would always fall on a surface of constant field strength. For a typical single source magnet, such a surface would be calculable, and would approximate an axially symmetric spheroid.

Figure 9:
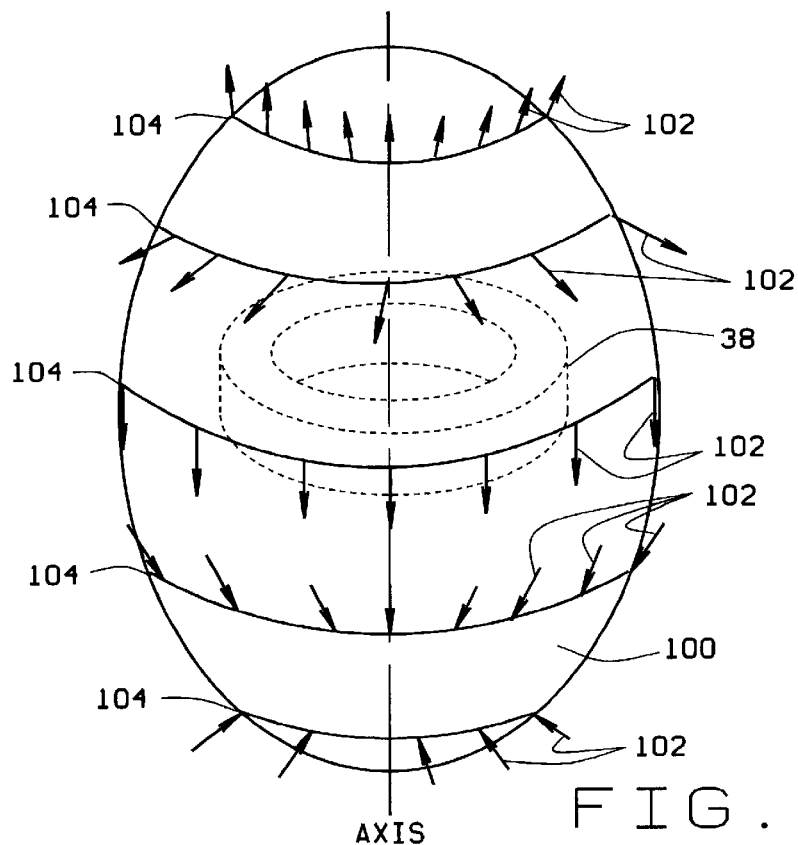
FIG. 9 is representation of the approximately spheroidal shape of a surface of constant field strength for a magnet having axial symmetry.

FIG. 9 illustrates a surface 100 of constant field strength for a source magnet 38, along with a few vectors 102 on each of several "latitude planes" 104. It is seen that on a given latitude plane the axial symmetry of the magnet assures that the field line vectors 102 make a constant angle with the surface 100, and also with the magnet axis. Each field line lies in a plane which contains the magnet axis. Thus changes in field direction, on the constant field surface, require some component of motion along a longitudinal line.

Once the relative locations of $V_1$ and $V_1'$ are determined, rotations are made in the "forward direction," $V_1$ to $V_1'$, by standard matrix means. For example, Goldstein equation (4–46) shows such a transformation using Euler angles ($\phi$, $\theta$, $\psi$) in one turn sequence convention. This reference also discusses several other such conventions. The particular rotation convention used for ($\phi$, $\theta$, $\psi$) in this invention is arbitrary, but once chosen for the initial calibration it must be retained. A convenient choice might use the axes of rotations provided by the articulation mechanism. "Reverse" rotations, say from $V_1'$ to $V_1$, are then given by an inverse matrix, Goldstein equation (4–47). It is to be understood that the angles ($\phi$, $\theta$, $\psi$) are not angles through which the source magnet will actually turn, but rather are used in the algorithm to calculate the transformation between a vector in the two reference frames. Instead, the actual magnet turns will consist of simple small vector rotations, with added translation if needed to maintain the vector position of the magnet tip 46 in the patient frame.

The movements of the source magnet for a proper turn are preferably first carried out "virtually" in a computer processor 22. Once the path for the movements of the source magnet is determined, execution of the path will require instructions to the controller 34 of the magnet articulation mechanism 36. Algorithms for calculating the angles and translational position of the magnet needed to provide a next V (i.e., a next B) are described below:

A. Once $V_1$ is located, the desired turn to $V_2$ is input by the physician according to one of the standard means of communicating to the processor system. Examples of methods of inputting desired turns are disclosed in U.S. utility patent application Ser. No. 09/020,798, filed Feb. 9, 1998 entitled "Device and Method for Specifying Magnetic Field for Surgical Applications", incorporated herein by reference, or co-pending U.S. patent application Ser. No. 09/370,067 filed Aug. 6, 1999, entitled "Method and Apparatus for Controlling Catheters in Body Lumens and Cavities", incorporated herein by reference.

B. The movement of the source magnet to effect the turn from $V_1$ to $V_2$ is determined. This is conveniently done with a computer processor. The angle by which the direction of the magnet tip 46 varies from the plane containing $V_1$ and $V_2$ is then determined. If this amount does not exceed a predetermined threshold for acceptable deviation, e.g., 5 degrees, then the articulation mechanism 36 can be operated by controller 34 under the direction of the computer processor 22 to make the determined movement of the source magnet 38. If the turn from $V_1$ to $V_2$ is small, for example, 10 degrees or less, it is likely that only one step of the turn is needed, as any coning during the turn will be small enough that it generally will not interfere with navigation. However, if the amount by which the direction of the magnet tip 46 varies from the plane of $V_1$ and $V_2$ by more than the predetermined threshold, then the turn is broken up into a number of sub-turns. Of course, sub-turns could be used automatically, without testing whether they are needed.

C. If subturns are employed, the final vector $V_2$ is labeled $V_n$, and a number of intermediate vectors $V_i$(i=2, 3, ..., n−1) are determined by the processor 22. One method of determining these intermediate vectors is to make an even-sized division of the angle of turn, constraining each individual vector to be in the plane formed by $V_1$ and $V_n$. Other methods of determining these intermediate vectors include unequal divisions of the turn angle based upon where the magnet tip direction deviates from the desired plane of the turn by more than the predetermined threshold, or some lesser value. Of course there are numerous other methods for determining the intermediate vectors.

D. The vectors $V_1$, $V_2$, ..., $V_n$ in the patient frame of reference are transformed to $V_1'$, $V_2'$, ..., $V_n'$, in the source magnet frame of reference by a pure forward rotation. In general, $V_1'$, $V_2'$, ..., $V_n'$ will not lie in a plane, even if $V_1$, $V_2$, ..., $V_n$ did. Each pair of angles, $V_1'$, $V_2'$, or $V_2'$, $V_3'$, etc. will form a plane, which can be determined as in equation (2) above. Resulting rotations $V_1$ to $V_2$, or $V_2$ to $V_3$, etc. will not generally lie in a single plane, but since these are small rotations they will have acceptable individual coning, by decision of step 2 above. Choice of the starting vector in the patient plane, however, will assure that the overall turn is nearly planar.

Figure 10:
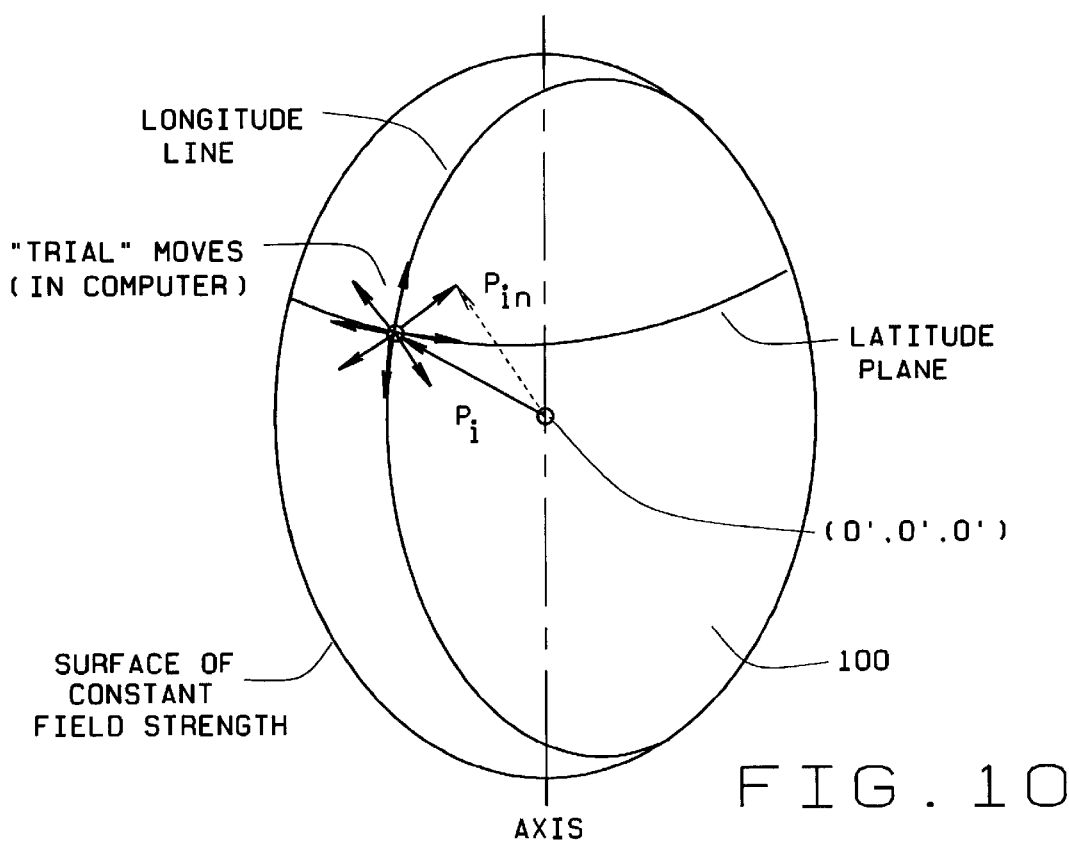
FIG. 10 is a diagram of a constant field strength surface showing several trial moves of the source magnet useful in visualizing the efficient movement of the source magnet.

E. The processor 22 then determines a movement of the magnet for each of the sub-turns. When the magnet makes a rotation from $V_i$ to $V_{i+1}$, the point on the constant field surface will in general move, i.e., translate relative both to (0', 0', 0') and to (0, 0, 0). Also, the magnet rotation needed to make this small turn, will not in general be uniquely determined, which is common with inverse problems. The processor will calculate such a translation for the small angle rotation $V_i$ to $V_{i+1}$, using a series of trial rotations in a plane tangent to the surface at the initial point, in the neighborhood of the vector $V_i$, as shown in FIG. 10. In general, each vector associated with a rotation shown in this frame, corresponds to a rotation and translation of the point in the patient reference frame. That is, as the field vector position in the magnet frame changes from $P_i$ to $P_{i+1}$ due to rotation in the magnet frame, the reverse transformed position in the patient frame will need in addition to translate if the original rotation in the patient frame [Goldstein equation (4–46)] is to transform back correctly. That means that the source magnet 38 must simultaneously be translated to maintain the magnetic field vector position constant in the patient frame. Only moves with some component along a longitude line will change the field vector direction. However, it will sometimes be found that the most efficient step for a small turn will also have some component of rotation along a latitude line, when account is taken of the transformation into patient coordinates. For each trial the processor will calculate the translation inferred in the patient frame. For the trial chosen as optimum, the magnet will have to make the inverse of this translation, in order to keep the vector location fixed in the patient frame.

F. The processor selects from the trial rotations one which is most efficient, i.e., the trial which requires the smallest translation of the magnet to accomplish the (partial) turn in the patient frame without a translation in the patient frame. A weighting algorithm can be developed based upon the "costs" of certain rotations over other rotations, certain translations over other translations, and of rotations over translations.

Practical articulators and magnet systems will have limited rotations, say 360 degrees or 720 degrees, because of leads, and other attachments. They also will have limitations of motions because of interference of the magnet and its accoutrements with the patient, with imaging equipment and imaging beams, or with other medical equipment. Such limitations can be transformed from the patient reference frame to the source magnet reference frame and entered into the processor 22 controlling the navigation as an exclusion region. Preferably the limitations can be entered as a series of vectors $X_1, X_2, \ldots, X_n$ describing a surface in the patient frame, which transform to $X_1', X_2', \ldots X_n'$ in the source magnet frame. These can be chosen with sufficiently small angular spacing as to provide a means of forming a smooth sheet of exclusion boundary in the magnet frame, which is used by the processor to execute limits on magnet motion.

When the magnet housing and accoutrements present a highly asymmetrical front toward the patient and interfering equipment, the exclusion sheet will be dynamic, i.e. a joint overlap of sheets for the patient region and for the magnet region will be needed to prevent interference.

G. The final and all intermediate step vectors ($V_2', \ldots V_n'$) will be calculated before the execution of a turn. When, in any turn, the final (or any intermediate) step vector falls beyond an exclusion limit, or near it, the processor 22 can choose to reorient the source magnet, using its symmetry, if helpful, to move safely away from incursion of the limit. Clearly, for safety the limit surface can have been chosen conservatively "inside" a true limit surface.

H. The processor 22 also confirms that the rotations will not cause the direction of magnet tip to vary from the plane of $V_1$ and $V_n$ by more than the predetermined threshold. If it does, the processor re-selects some or all of the intermediate vectors ($V_2', \ldots V_{n-1}'$), and repeats the process.

I. The processor 22 will then cause the articulating mechanism 36 to turn and/or translate the source magnet 38 successively through the angles from $V_2'. \ldots, V_n'$, which will turn the angle in the patient from through $V_2, \ldots V_{n-1}$ to $V_n$.

Common matrix transformations can be used for conversion between the patient reference frame and the source magnet reference frame. One technique includes the steps of:

1. Characterize the field of the source magnet 38 by measuring it over the sample volume of interest at sufficient resolution that interpolation will not yield significant errors.
2. Putting the source magnet field information into a computer function $B_m(x_m, y_m, z_m)$ x', y', z' as shown in FIG. 8), or equivalent lookup table, where $x_m$, $y_m$, and $z_m$ are expressed in magnet coordinates and $B_m$ is the magnetic field vector.

3. Compute the transformation matrix $T_{mp}$ for converting a general vector B from magnet to patient coordinates.
4. Invert this matrix to $T_{mp}^{-1}$.
5. Compute $x_m$, $y_m$, $z_m$ by feeding $T_{mp}^{-1}$ into a general minimization function that moves around the magnet on its constraints (e.g., where there are three degrees of freedom, 2 rotations and 1 translations) and using a forward calculation function:

$$B_p(x_p,y_p,z_p)=T_{mp}^{-1}B_m(x_m,y_m,z_m)$$

Such a routine would rapidly converge unless the magnet shape and/or shielding presented fields which are pathological (not monotonic in the vicinity of the required components). Such magnet designs should be avoided. Where there are more degrees of freedom, this will involve searching over the surplus degrees of freedom to minimize the required movement (rotation and translation) of the source magnet.

Navigating with a Single Magnet

When the determination of magnet rotations for a safe turn has been made by the previously described steps, instructions to the chosen robotic articulation mechanism 36 for magnet positions and rotations to be achieved in a turn, or partial turn, are needed. These algorithms can be put into two categories, those involving magnets with axial symmetry and those without axial symmetry. In addition, it is possible to have practical modalities of operation for symmetrical magnets which take advantage of the symmetry to simplify the magnet articulations, and to use fewer numbers of degrees of freedom in them. Three preferred modalities will be described: (A) is an efficient, highly specific 3-degree of freedom navigation for an axially symmetric magnet, with a flow chart for the inversion of the field in the source magnet coordinates to the field in the patient coordinates shown in FIG. 13; (B) is a more general 3-degree of freedom method which covers the making of turns; and (C) is a general 5-degree of freedom algorithm by which the greater articulation flexibility provides for better handling of exclusion boundaries in which the magnet cannot move.

(A) 3-degree of Freedom Navigation for an Axially Symmetric Magnet

It can be seen that one of ordinary skill in the art can extend the specific information of this example (A), especially the explicit definitions and diagrams, in a manner to provide different versions of the present means, or any more general modality of navigation by using different numbers of rotations and/or translations.

Figure 11:
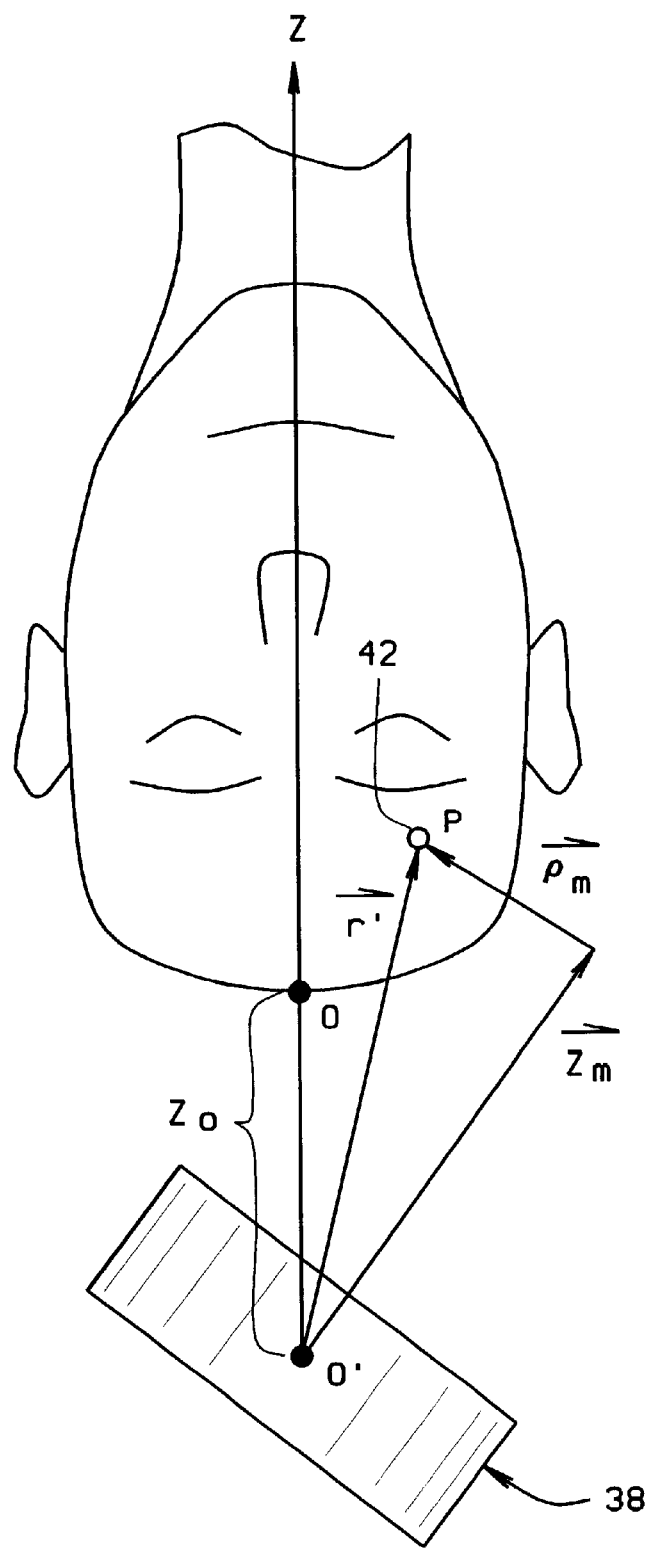
FIG. 11 is a schematic view a patient and a source magnet, illustrating coordinates and vectors useful in navigating.

FIG. 11 is a diagram showing a patient, a single magnet source of external magnetic field, the location for a small magnet tip to be guided in a medical procedure, and the definition of a few of the coordinates and vectors to execute the above-described type of navigation in one preferred embodiment. At the magnet tip location or operating point 42 specified by r' (also by point P) a magnetic field B is to be applied with given magnitude and orientation to create a turn.

Figure 12:
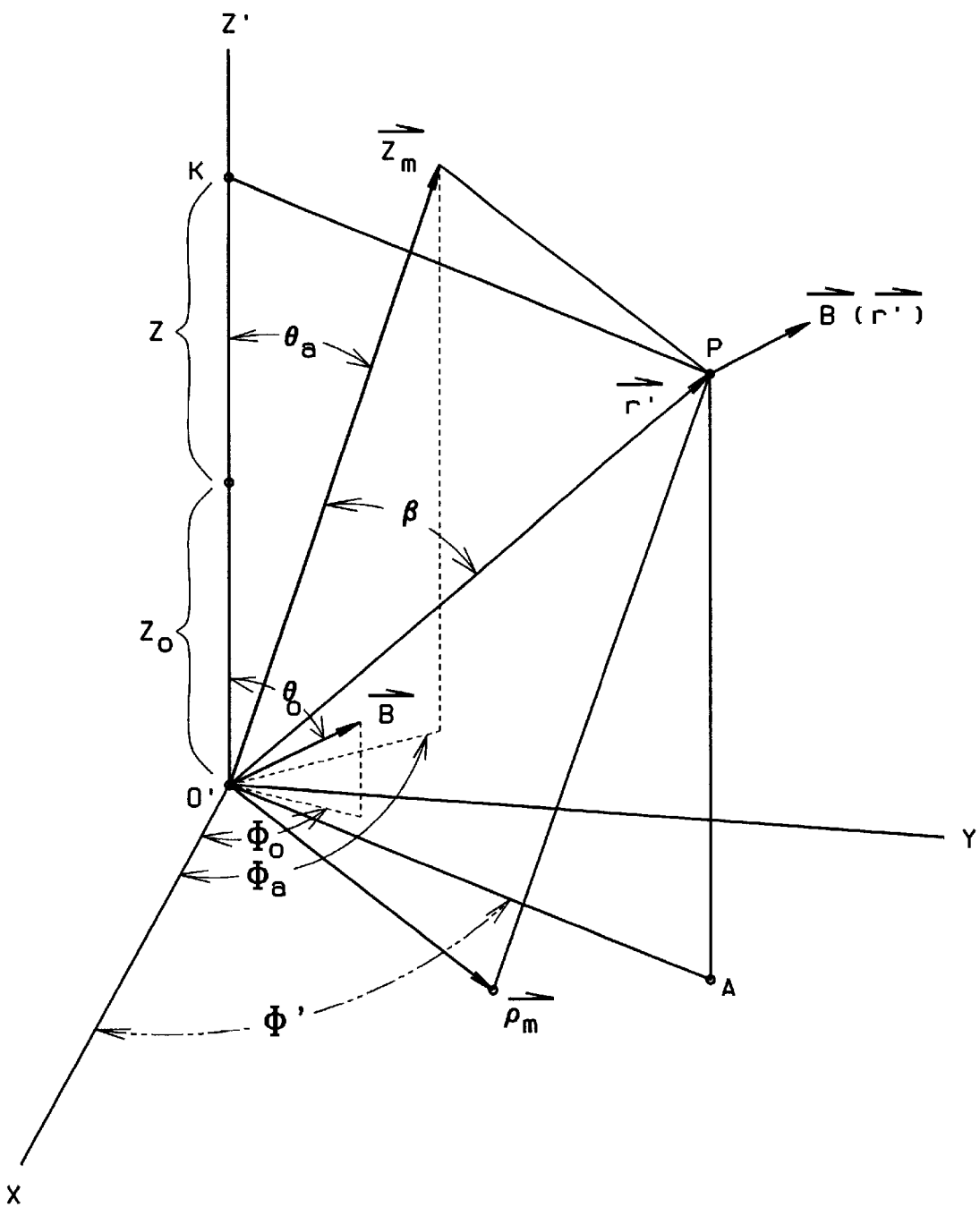
FIG. 12 is diagram of the coordinates for the source magnet, shown in FIG. 11 illustrating the planes of rotation.

FIG. 12 shows additional useful parameters and defines coordinates for the single magnet and field point (the operating point represented by position vector r') at which the field vector B is to be specified, and which is to be provided by the articulated magnet. It also shows planes which make the geometric attributes of this motion easier to visualize.

The magnet position in this three degree-of-freedom problem is uniquely specified by the offset $z_o$ (distance of the center of the coil from the closest point of patient anatomy), and the polar and azimuth angles made by the magnet symmetry axis $z_m$ relative to the translated patient coordinate system (x, y, z') system.

For a coil having axial symmetry this method shows how to make the search for one degree of freedom trivial by using an analytical expression for one of the variables. This method takes advantage of the fact that the field vector B must lie in the plane defined by the vectors $z_m$ and $\rho_m$, due to the cylindrical symmetry of the source magnet (either a coil magnet or a permanent magnet).

Referring to FIGS. 11 and 12 for a supine patient, the y-z plane is horizontal, x is vertical, y is horizontal to the patient's right, and z is along the patient body axis. A second set of coordinates is used, where x, y, z' with origin O' is displaced along z by an amount $z_o$ from the patient origin O shown in FIG. 11. Thus the x,y,z and x,y,z' planes are vertical and are perpendicular to the patient body axis, at the top of the patient's head and through the magnet center, respectively.

The operating point 42 (or P) is at r' in the x, y, z' coordinate system. $\theta_o$, $\phi_o$ are the spherical polar coordinates of B in a system with polar axis along z', and azimuthal angle measured from the x,z' plane. In FIG. 12, B is shown both at its true location P and at the origin O' where these angles can be shown clearly. $\theta_a$, $\phi_a$ are the polar and azimuthal angles of the magnet axis $z_m$, in the same spherical polar coordinate system as the patient frame, with the polar axis along z and the azimuth measured in the x,y plane and relative to the x-axis.

$z_m$, $\rho_m$ are the cylindrical coordinates of the operating point 42 in an axially symmetric magnet coordinate system, corresponding to the vectors $z_m$, $\rho_m$. The field point at x, y, z', specified as the vector r', is identified as P. The point of intersection of a line parallel to the z-axis and passing through P with the line of projection of r' on the x, y plane, is identified as A. The polar angle of r' in patient coordinates is identified as $\theta$. The polar angle of r' in magnet coordinates is identified as $\beta$. The point on the z-axis at $z_o$+z is identified as K. There are three parallelograms defining three planes: The first, O'APK is a parallelogram which forms a plane perpendicular to the x, y plane and going through both the z-axis and the field point P. r' falls in this plane. The rotation of this plane about the z-axis is by angle $\phi'$ with respect to the x-z plane. The second, O'$\rho_m$P$z_m$ is a parallelogram which forms a plane containing the field point P and the axes $z_m$ and $\rho_m$. r' also falls in this plane and therefore this vector forms the axis of intersection of the two planes. By its definition $z_m$ is the projection of r' on the axis of the coil. Not only the field point P, but the field vector B lies in this plane, which is an axial plane of the magnet (a plane containing a complete field line and the magnet axis). r', and therefore both parallelograms, rotate about z as the field point changes in azimuth in the patient coordinates. The second parallelogram is in general tilted relative to the first. The third plane is the plane formed by B and the line PA. This plane is in general oblique to the first and second planes.

As defined, $\phi_a$ is a precession angle of the magnet axis, the azimuthal rotation about z (measured from the x,z plane) of the line of the projection of vector $z_m$ representing the magnet axis, on the x-y plane.

The algorithm is implemented in the following steps (derivation and details are given later):

1. Specify coordinates (x, y, z) of a field point in the navigation volume of the patient.
2. Specify the magnitude of the desired magnetic field B, and a desired accuracy for this magnitude.
3. Specify the polar and azimuth angles $\theta_o$ and $\phi_o$ of the desired B vector.
4. Specify an accuracy for the dot product between the specified and computed B unit vectors.

5. Search on the magnet azimuth coordinate $\phi_a$ as follows:
   a. For each $\phi_a$, search on the magnet offset, $z_o$.
   b. For each pair $\phi_a$, $z_o$, calculate the magnet polar angle, $\theta_a$, which is required to insure that the B vector lies in the z–r' plane.
   c. Continue the search on the offset $z_o$ until the computed coil field magnitude is equal to B to within the desired accuracy.
   d. Using this offset, and the set of azimuth and polar magnet angles, compute the B vector at the field point
   e. Form the dot product between the computed and specified B vectors. Form the dot product of unit vectors by dividing by the vector magnitudes.
   f. When this dot product is equal to unity to within the specified accuracy, the inverse calculation is complete
6. Calculate the changes in $z_o$, $\phi_a$ and $\theta_a$ from their present positions.
7. Calculate a sequence of these variables which will provide the changes proportionately.
8. Send the sequence to the magnet articulation device 36 to effect the determined movement of the source magnet 38.

In summary, the method searches magnet azimuth and magnet offset, computes a polar angle that insures that the B vector lies in a plane containing the magnet axis and the field point vector, selects an offset that insures the correct magnitude of B, and completes the azimuth search when the computed and specified B vectors are aligned in space.

The derivation and details of this Example A are as follows: The vectors r', $z_m$, and B are given in their polar representations by:

$$r'=r'[\sin\theta'\cos\phi' i+\sin\phi' j+\cos\theta' k] \quad (5)$$

$$z_m=z_m[\sin\theta_a\cos\phi_a i+\sin\theta_a\sin\phi_a j+\cos\theta_a k] \quad (6)$$

$$B=B[\sin\theta_o\cos\phi_o i+\sin\theta_o\sin\phi_o j+\cos\theta_o k], \quad (7)$$

The angles of the position vector r' are given in terms of its Cartesian coordinates by:

$$\phi'=\tan^{-1}(y/x) \quad (8)$$

$$\theta'=\tan^{-1}\{[\sqrt{(x^2+y^2)}]/(z+z_o)\}, \quad (9)$$

and, $$r'=\sqrt{[x^2+y^2+(z+z_o)^2]}. \quad (10)$$

The polar and azimuth angles $\theta_a$ and $\phi_a$ of the magnet axis are unknowns to be determined. The polar and azimuth angles of the B vector, $\theta_o$ and $\phi_o$, are specified by the user, or are calculated from its Cartesian representation.

The polar angle $\theta_a$ can be computed mathematically in terms of the other angles by imposing the condition that the B vector lie in the $z_m$–r'–$\rho_m$ plane. This condition is necessitated by the symmetry of the coil. It is stated mathematically as the null dot product of B with a vector perpendicular to that plane $$B\cdot(z_m\times r')=0. \quad (11)$$

Insertion of the defining equations (1) to (3) into (7), and noting that the magnitudes of the vectors drop out, we have an equation which can be solved for the tangent of the polar angle:

$$\theta_a=\tan^{-1}\{[\sin\theta'\sin\theta_o\sin(\phi'-\phi_o)]/[\cos\theta_o\sin\theta'\sin(\phi'-\phi_a)+\cos\theta'\sin\theta_o\sin(\phi_a-\phi_o)]\} \quad (12)$$

The field components relative to the magnet are given by:

$$B(r')=B_\rho(\rho_m,z_m)\rho_m/\rho_m+B_z(\rho_m,z_m)z_m/z_m \quad (13)$$

where a numerical coil field algorithm computes $B_\rho$ and $B_z$, given the coordinates $z_m$ and $\rho_m$. From FIG. 12 the magnitude of the z and $\rho$ components of the vector r' are:

$$z_m=r'\cos\beta \quad (14)$$

$$\rho_m=r'\sin\beta, \quad (15)$$

where the angle $\beta$ is measured in the $z_m$–r'–$\rho_m$ plane and can be found from vector operations to be:

$$\cos\beta=\sin\theta_a\sin\theta'\cos(\phi_a-\phi')+\cos\theta_a\cos\theta' \quad (16)$$

$$\sin\beta=\sqrt{(1-\cos^2\beta)}. \quad (17)$$

The computed magnitude of the field in magnet components is $$B=\sqrt{(B_\rho^2+B_z^2)}, \quad (18)$$

and this expression is used in the algorithm to search the magnet offset, $z_o$, where equations (12) to (17) are used to compute equation (18) for each value of $z_o$.

Finally, the search on the magnet axis azimuth is terminated when the specified B vector and the B vector computed from Equation (13) are aligned in space to within a given accuracy. Appropriate expressions for the unit vectors in terms of the patient Cartesian coordinates are:

$$z_m/z_m=\sin\theta_a\cos\phi_a i+\sin\theta_a\sin\phi_a j+\cos\theta_a k \quad (19)$$

$$\rho_m/\rho_m=(r'-z_m)/\rho_m=[(\sin\theta'\cos\phi'-\cos\beta\sin\theta_a\cos\phi_a)/\sin\beta]i+[(\sin\theta'\sin\phi'-\cos\beta\sin\theta_a\sin\phi_a)/\sin\beta]j+[(\cos\theta'-\cos\beta\cos\theta_a)/\sin\beta]k \quad (20)$$

The specified and computed unit vectors are obtained from equations (7) and (13) by dividing by the specified field magnitude and field magnitude computed by Equation (18), respectively. When their dot product is equal to unity, within the specified accuracy, the azimuth search is complete.

The solution offset, polar and azimuthal angles $z_o$, $\theta_a$, and $\phi_a$ are then used to articulate the magnet to acquire the desired field B.

Figure 13:
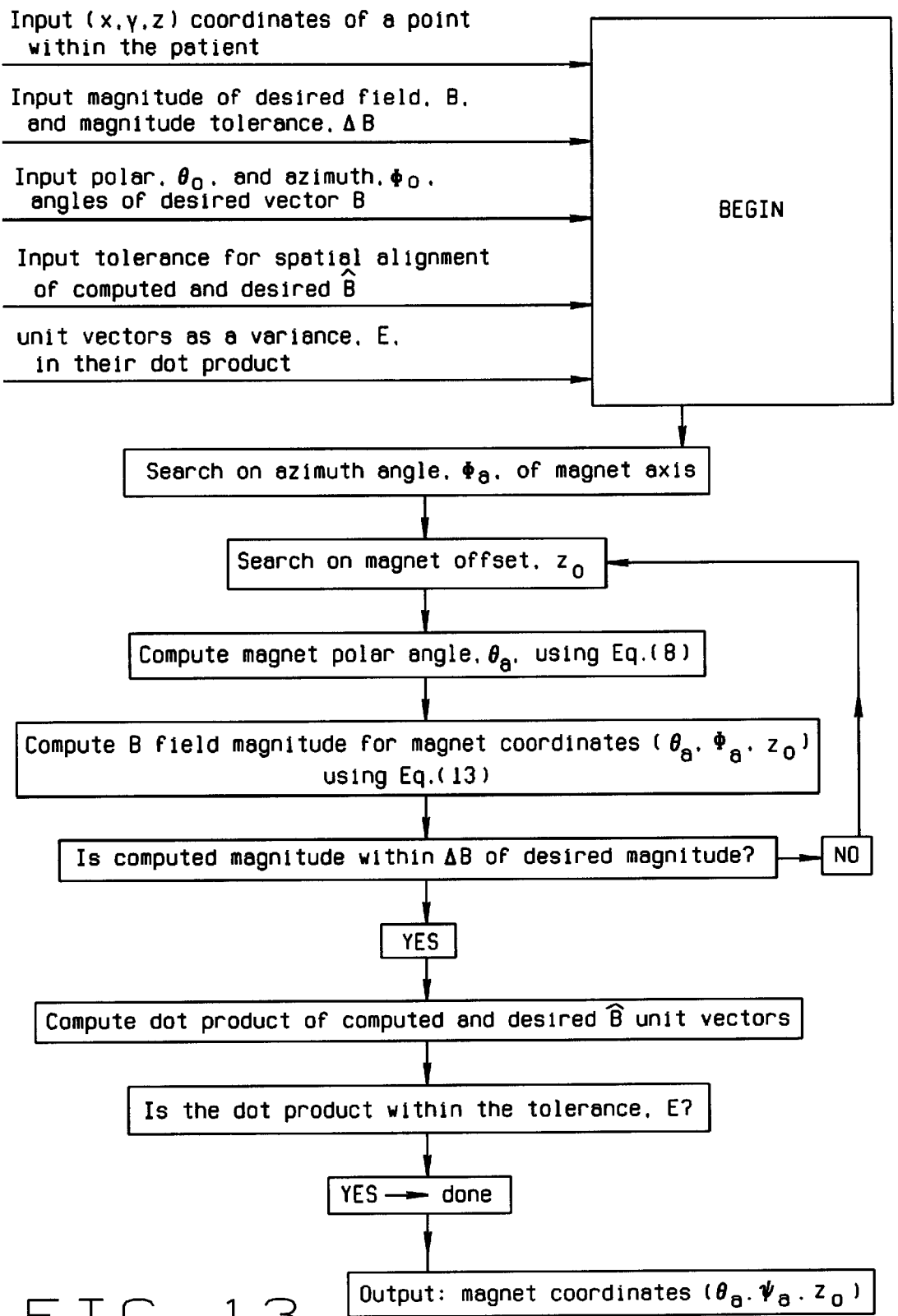
FIG. 13 is a flow chart of the navigation inverse algorithm.

FIG. 13 is a flow chart of a program which executes the algorithm just presented to provide the inverse calculation for articulating a magnet having axial symmetry. A preferred embodiment of a more general search which allows an incremental proper rotation of a field vector is presented below in example (B). An outline of an embodiment for a general 5-degree-of-freedom search is also presented below in example (C). One versed in the art will see how to modify these to provide inversion algorithms to articulate a magnet with any number of degrees of freedom greater than 3.

(B) Navigation with 3-degree of Freedom Searches

The algorithm outlines a method which operates directly with transformation matrices, t requires a full 3-parameter search.

Magnet Insertion

1. Locate the current magnet tip location, r' (i.e. the operating point 42 or P) in the patient frame.
2. Input the desired starting field direction, B, in patient coordinates.
3. Using appropriate transformations, and a search sequence, calculate the necessary magnet axis rotational angles, $\phi$ and $\theta$, and translation axis position to achieve B at r'.

4. Execute magnet axis rotations φ and θ.

5. Execute translation to calculated position.

After the source magnet has been inserted

1. Locate the current magnet tip location, r', in the patient frame.
2. Translate the magnet along the z-axis to bring the operating point 42 or P where the magnet tip 46 is located, to the desired field strength line of the magnet.
3. Calculate the desired new magnetic field direction $B_2$ in patient reference frame at the operating point P or 42 where the magnet tip 46 is located.
4. Input the new desired magnetic field direction, $B_2$, in patient coordinates.
5. Create a set of vectors in the patient reference frame that link $B_1$ to $B_2$ at the operating point 42 or P that lie in the plane created by $B_1$ and $B_2$.
6. Calculate the necessary magnet axis rotations, φ and θ, and translation that produces the set of vectors found in step #5.
7. Execute movement with the 3 variables synchronized.

Figure 7A:
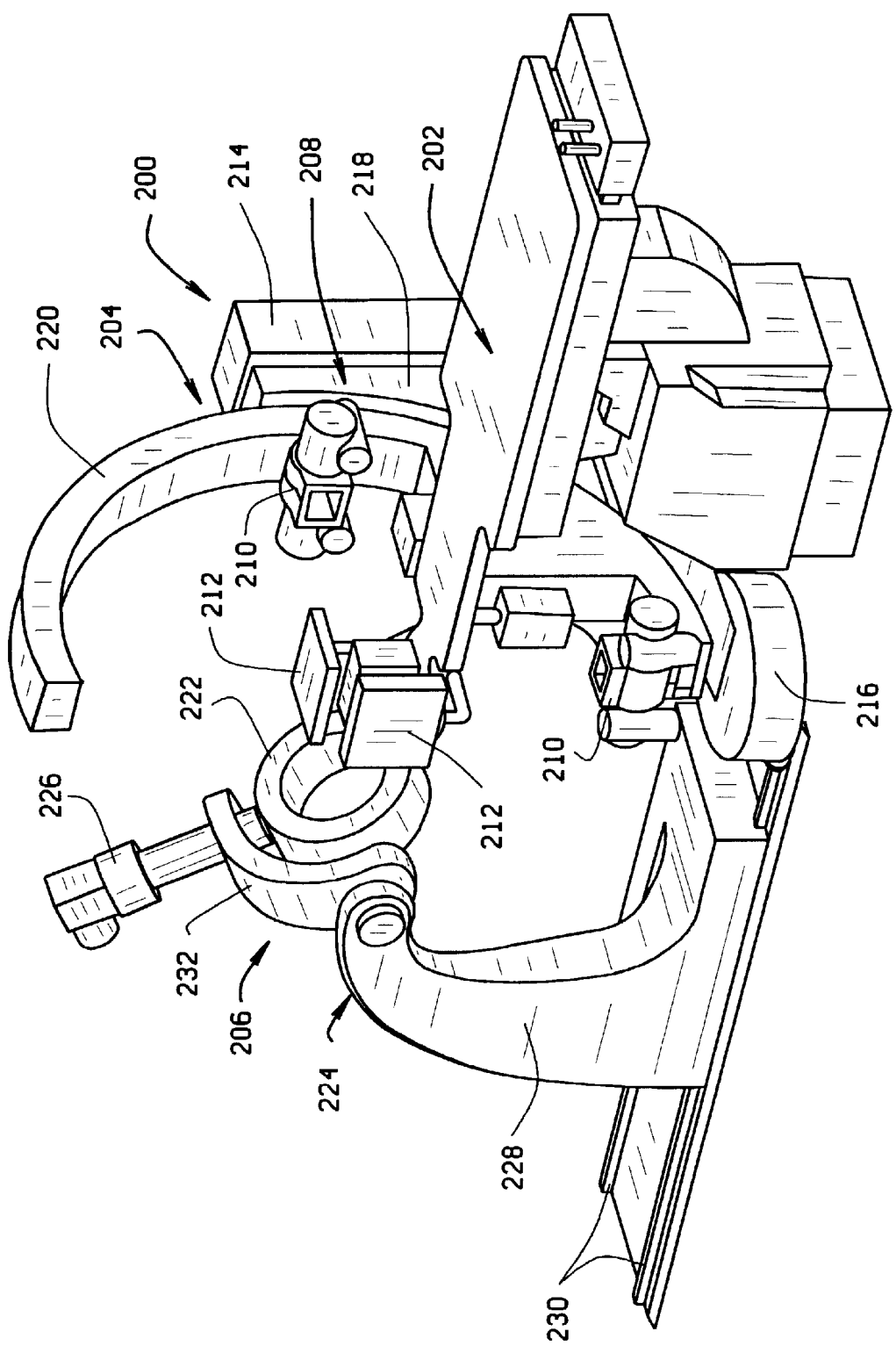
FIG. 7A is a perspective view of a single magnet system having three degrees of freedom, for implementing the method of the present invention.
Figure 7B:
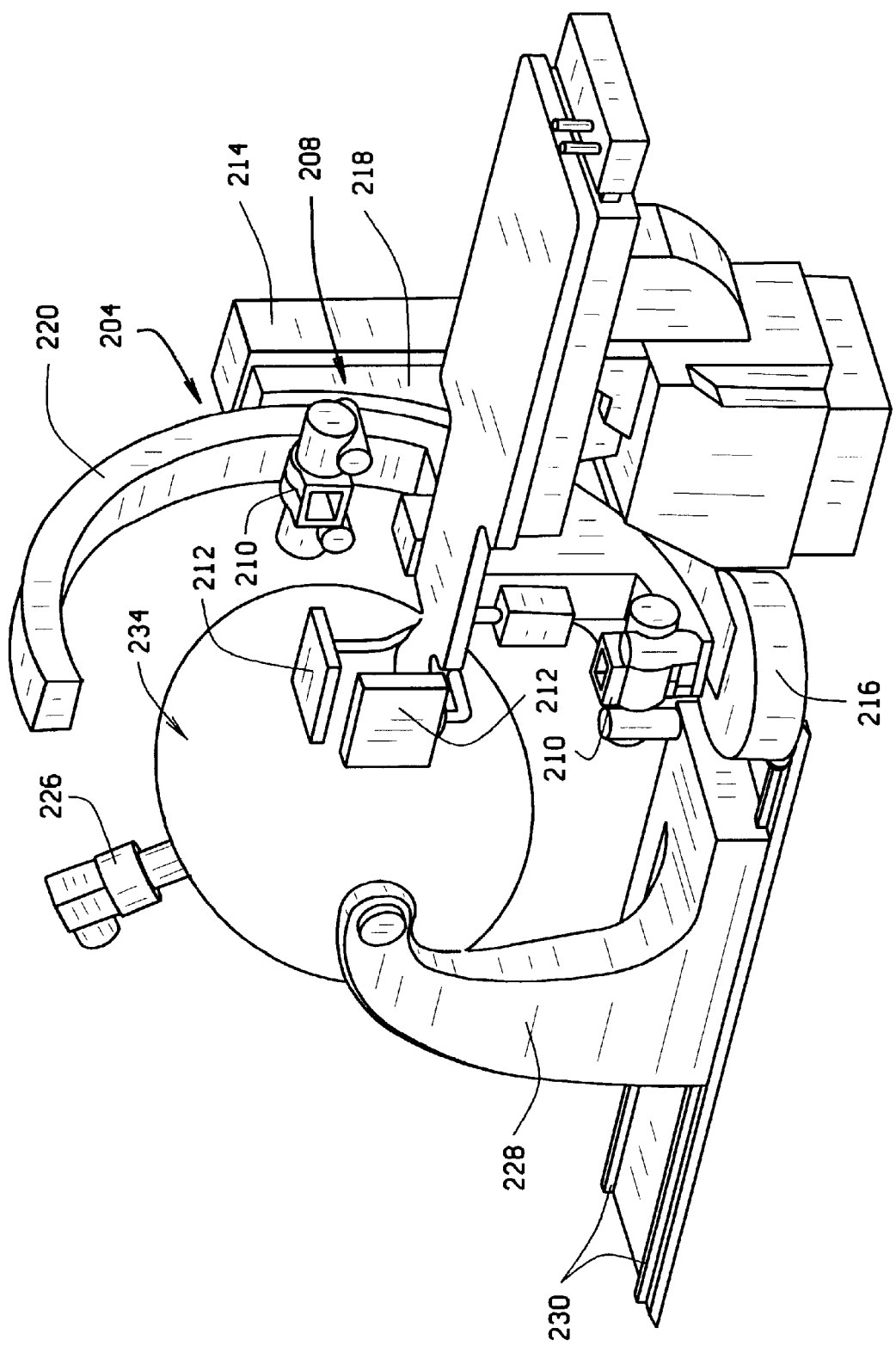
FIG. 7B is a perspective view of the system shown in FIG. 7A with the surface of constant magnetic field strength superposed thereon, illustrating some of the exclusion zones around which the magnet must be maneuvered.

In a practical device for implementing the method of example (B), such as the one shown in FIGS. 7A and 7B, the azimuthal rotation might be limited to 360°, the polar rotation limited to 180°, and the Z-axis translation might be limited to 8.5 inches to about 14.5 inches. Motion is selected to avoid possible problem with navigation due to rotational stops in azimuthal direction.

(C) Navigation with 2 Rotational and 3 Translational Degrees of Freedom

Figure 7C:
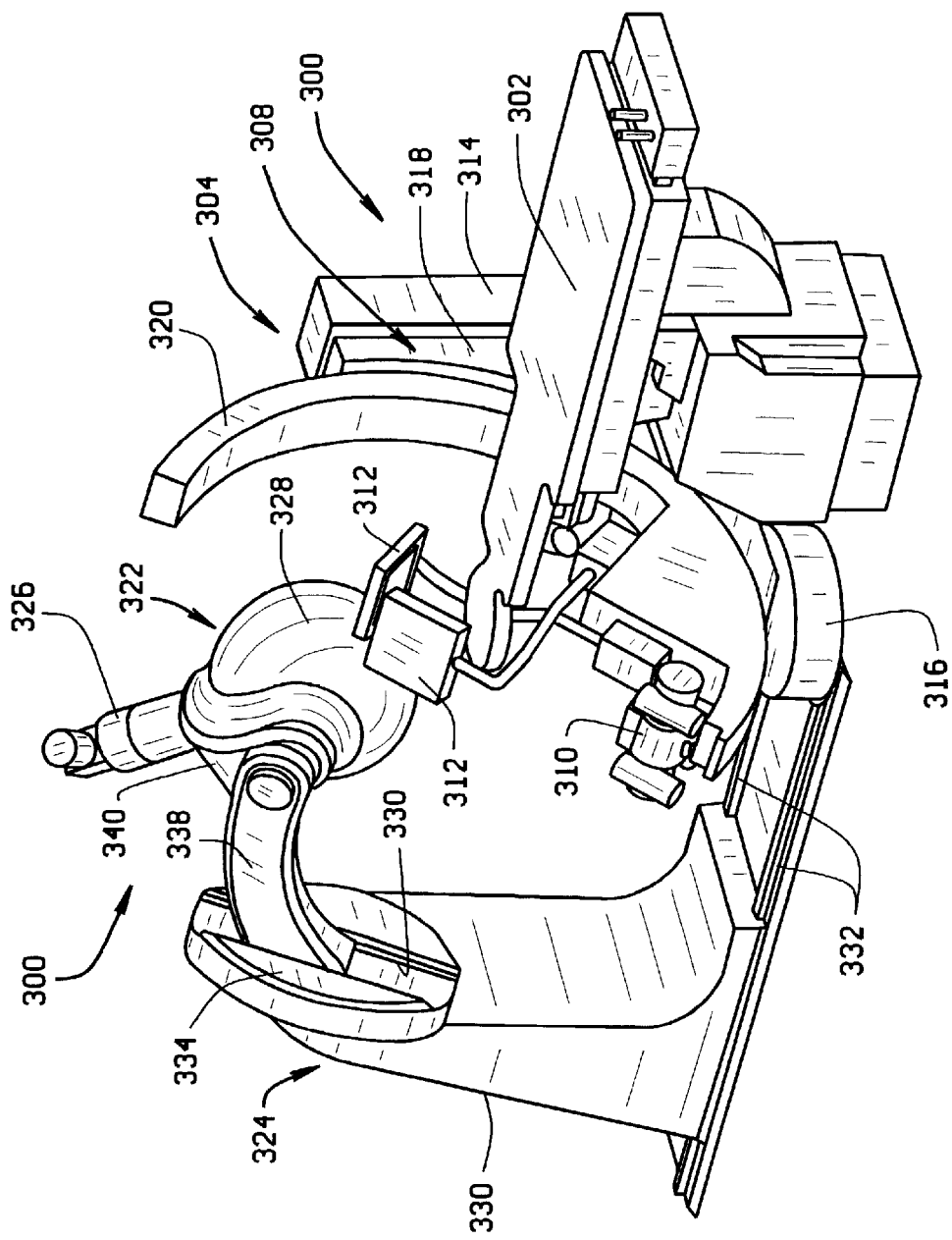
FIG. 7C is a perspective view of a single magnet system having five degrees of freedom, for implementing the method of the present invention.
Figure 7D:
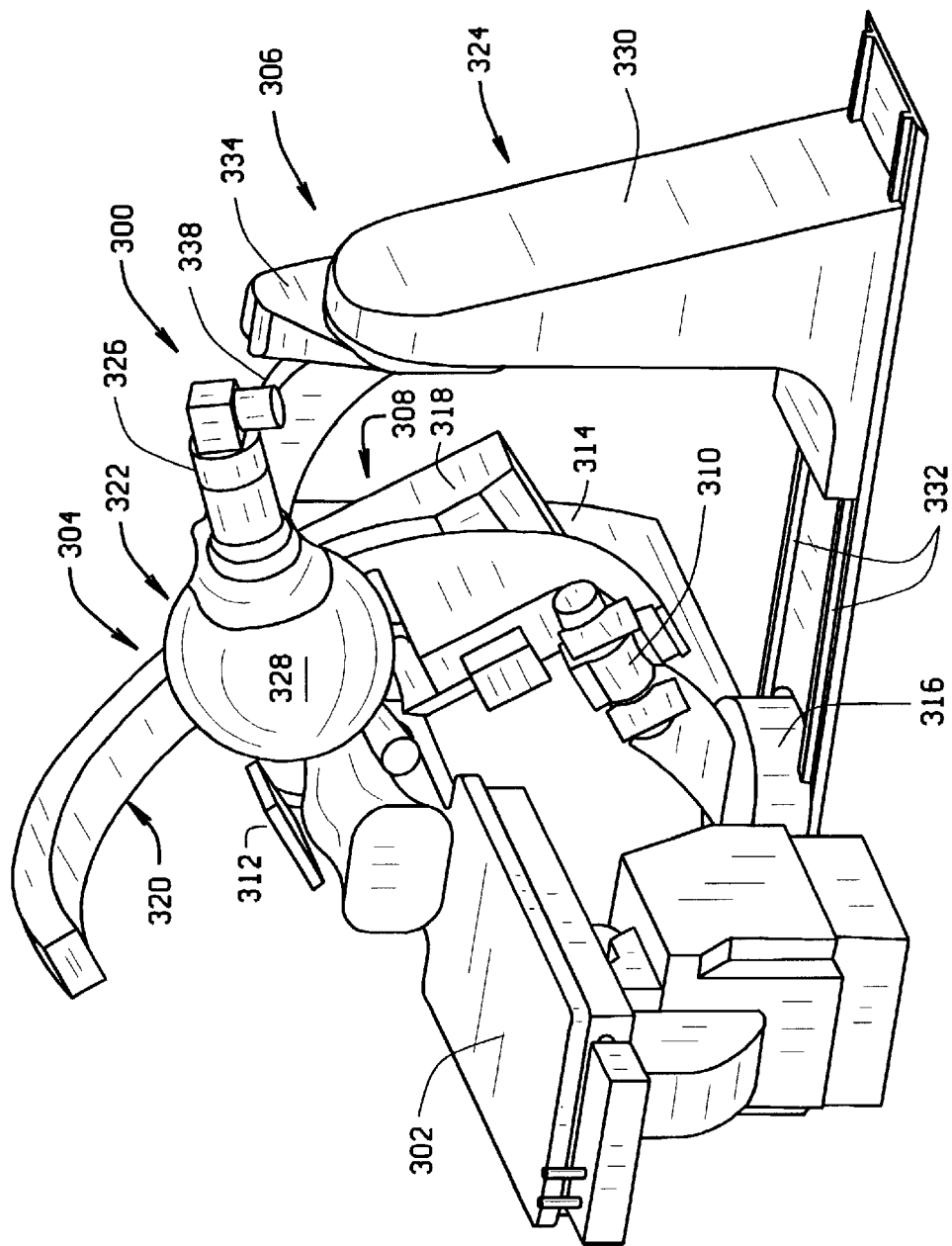
FIG. 7D is a perspective view of the single magnet system shown in FIG. 7C, from a different angle.

This outlines a method of using two additional translational motions which can give flexibility to avoiding interferences with patient and imaging equipment and beams. Such a method might be implemented by the device shown in FIG. 7C. By choosing specific x and y axis translations at the outset, the problem again becomes completely determined. If other constraints are more valuable in a specific application, these can be replaced.

1. Locate the current magnet tip location, P
2. Translate in the x y plane (x-axis and y-axis) such that the tip position and the center of the magnet coil define a line parallel to the z-axis of translation.
3. Translate along the z-axis to bring the current tip location, P, to the desired field strength line.
4. Calculate the magnetic field direction, $B_1$, at the tip location P.
5. Input the desired new field direction, $B_2$.
6. Create a set of field vectors that link $B_1$ to $B_2$ at P, and which lie in the plane of $B_1$ to $B_2$.
7. Calculate the necessary magnet rotations, φ and θ, and translation (z-axis only), for the set of vectors created in step 6.
8. Execute source magnet movement.

Use of Gradients

Navigation in accordance with this invention can be conducted in such a way as to use the source magnets to pull the medical device in addition to orienting the distal end of the medical device. Magnetic force is generated by the rate of change of magnetic field strength with position. This is commonly called a "magnetic gradient" even though a vector magnetic field does not have a gradient in the usual mathematical sense. As is well known to one of ordinary skill in the art, a magnetic field is a vector field, and a gradient operates only on a scalar field, that is a scalar function of position. What is usually meant by gradient is not gradient of the magnetic field, but the gradient of a scalar product of the magnetic moment vector m of the tip, and the magnetic field vector B at its location, i.e., (m·B). What is intended here, and generally in magnetic work, is the application of the force equation $$F = \Delta(m \cdot B) \quad (21)$$

Assuming a small magnetic tip 46, the moment can be treated as a point. This assumption is adequately met when the magnetic field changes over a distance appreciably larger than the size of the magnet tip. Thus the gradient operator acts on the scalar product m·B, the position dependent product of the magnet tip moment projected on the field B, at any given point. The direction of this force need not be along either the field direction B or the direction of the moment m. Rather it is in the direction in which the product m·B changes most rapidly.

Figure 14:
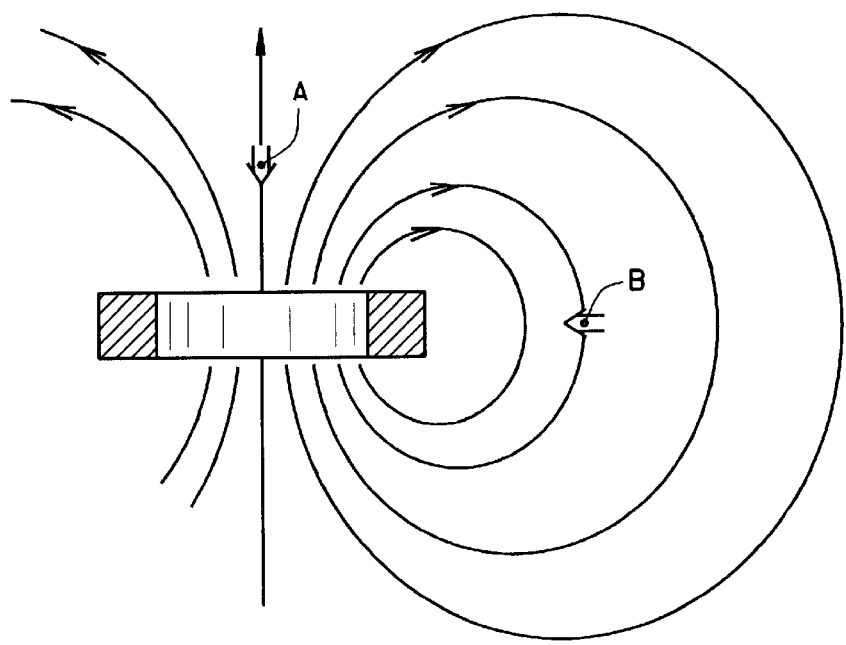
FIG. 14 is a cross sectional view of a typical coil source magnet 38 showing a number of its magnetic field lines, and illustrating the gradient direction in two different locations.

It is the purpose of this aspect of the invention to navigate a magnetic medical device with a magnet tip safely to a location and orientation in a patient so that the magnetic gradient which falls at that point will pull the tip in a desired direction. FIG. 14 shows a cross section containing the axis of a typical coil source magnet 38 with a number of its magnetic field lines. The arrows on the field lines show the direction of the magnetic field B at points along each line. In addition, the gradient of the field is shown in two locations, at points A and B, by double arrows. The directions of the arrows show the directions that a free small magnet would be pulled at those two locations. The direction of pull on a free magnet is in the direction in which the field lines are becoming denser, which is also the direction in which the field is increasing in strength. This is because a free magnet will align its moment with B, and remain aligned as it is pulled.

Thus the product m·B becomes simply the arithmetic product of the magnitudes of the two vectors, mB. But in practice a small magnet tip 46 on a magnetic medical device is not totally free, rather it is somewhat restrained by the device with which it is associated, as well as any surrounding tissue with which it is in contact. For example, catheters, guidewires, and electrodes etc. all have inherent stiffness that would restrain the alignment of the magnet tip with the field direction, in which case the product m·B will be somewhat smaller than mB, which is the maximum possible value.

In FIG. 14, a free magnet tip 46 at point A will be oriented with its moment aligned along the field which is along the axis of the source magnet 38, and the magnet will be pulled along the same direction. This is the "longitudinal gradient" or alternatively the "longitudinal field." It is also sometimes called an "axial gradient." At point B the free magnet tip 46 will have its moment m aligned along B and therefore parallel to the magnet axis, but the gradient will pull the magnet tip towards the source magnet as shown by the arrow, i.e., perpendicular to the source magnet axis. This is called a "transverse gradient," or alternatively a "transverse field." In some medical applications (e.g., pulling a linear electrode to an inner wall of a heart chamber, or pulling magnetic embolic material more smoothly towards an inner wall of an aneurysm) such a transverse gradient has been found to be advantageous.

According to this aspect of the invention, the magnetic navigation is supplemented by the application of the magnetic gradient. In some instances the application of the magnetic gradient assists in navigation, in other instances, the gradient is not applied to assist navigation, but to otherwise exert a pulling force on the magnetic medical device.

There are many instances where it would be desirable to exert a pulling force after a magnetic medical device has been navigated to a particular position in the body. For example, in the case of treating aneurysms, a magnetic pulling force could be applied after navigation of a magnet tip to a given location, for pulling magnetic embolic materials into an aneurysm. (The magnetic medical device may or may not be removed from the area before applying the pulling force). Either a transverse or longitudinal gradient may be used. If no subsequent navigation or significant turning of the orientation of the magnetic medical device is required, the computer processor 22 which controlled the initial navigation will have information not only about the orientation of the magnet tip 46, but about the orientation of the source magnetic field and gradient. That is, the processor will have information whether, at the operating point 42, the gradient is transverse or longitudinal. According to this aspect of this invention, the physician will, at the start of the procedure, input the desired method of using the gradient, and therefore at the completion of navigation (and after removal of the magnet tip, if necessary) the source magnet 38 will be oriented so that the gradient is in the desired direction.

At this point, a gradient must be established in the desired direction of pulling (e.g., the back wall of an aneurysm in an embolization procedure, or the wall of a heart chamber in an EP (electrophysiology) procedure). The processor 22 will have information about the current state of the magnetic field and gradient. Given the desired state of the relative directions of magnetic field and gradient, the processor can determine and direct a movement of the source magnet for the purpose of changing the direction of the gradient relative to the direction of the field, or vice versa. This relative movement between gradient direction and field direction is called a "gradient turn".

Figure 15A:
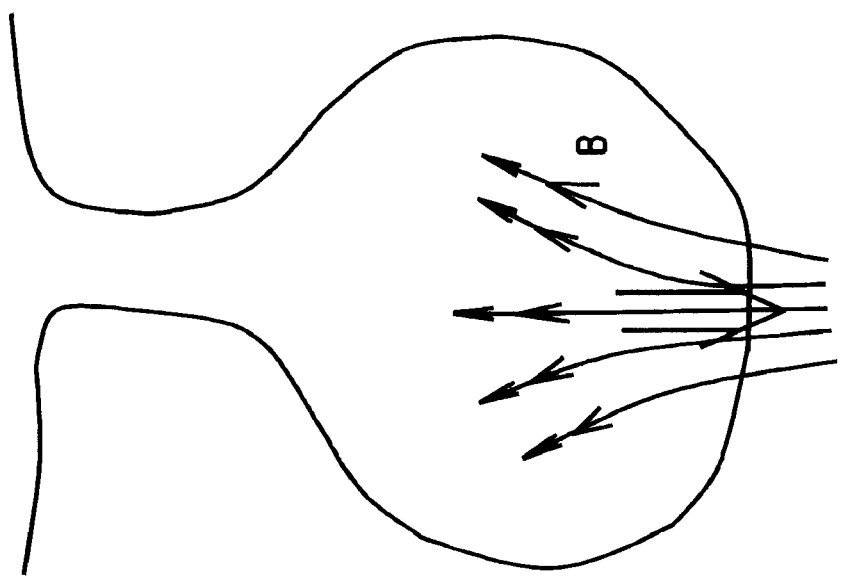
FIG. 15A is a cross-sectional view of an aneurysm, showing the relative orientations of an applied magnetic field and an applied magnetic gradient before a gradient turn.
Figure 15B:
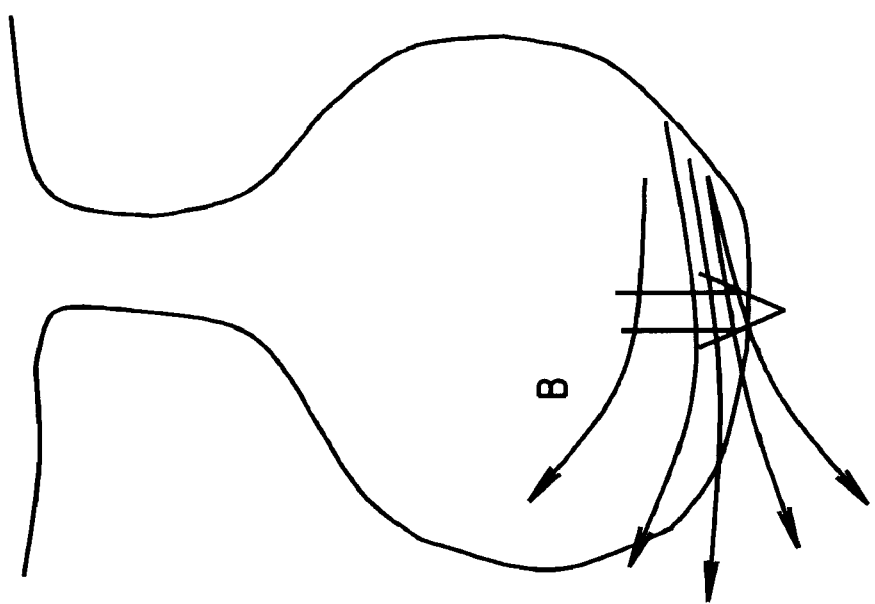
FIG. 15B is a cross-sectional view of the aneurysm, showing the relative orientations of an applied magnetic field and an applied magnetic gradient after a gradient turn.

FIG. 15A shows a cross section of an aneurysm with a magnetic field B represented by field lines pointing away from the back wall of the aneurysm, and a magnetic gradient represented by a double arrow, pointing toward the back wall of the aneurysm. In certain embolization procedures, it is desirable that the applied magnetic field be parallel to the neck of the aneurysm and perpendicular to a magnetic gradient that is oriented toward the back wall of the aneurysm. This builds a layered embolism in the aneurysm. As shown in FIG. 15B, after a gradient turn the magnetic field B represented by field lines pointing parallel to the neck of the aneurysm, is now perpendicular to magnetic gradient, represented by the double arrow, pointing toward the back wall of the aneurysm. While it is apparent from FIG. 14, and equation (21) what the gradient direction will be at these starting and ending locations, it is not apparent how the field and gradient directions relate at the intervening locations, nor how to use equation (21) to determine the gradient changes during that transition. The execution of a "gradient turn" above, will require a knowledge of the projection of B on m.

The requirement, then, is for the processor 22 to determine the movements of the source magnet 38 necessary to perform the gradient turn in the coordinate system of the patient. FIG. 14 shows a gradual change in the spacing of lines moving from a longitudinal gradient at point A to a transverse gradient at point B. That is, there can be a gradual change in the gradient of the scalar product m·B since m is fixed in magnitude and the line spacing is proportional to the magnitude of B. As discussed above, the navigation program implemented by the processor contains either an equation or a lookup table for the source magnetic field B of the magnet in the source magnet coordinate system. The location of the magnet tip 46 in the patient coordinate system is transformed into the source magnet coordinate system as described in earlier, so that B is known at the operating point 42 in the patient coordinate system from a further inverse transformation. The force F from equation (1) is determined from this information, knowing m, for the current source magnet position and orientation, and for a series of trial rotations and translations. The only additional requirement is knowledge of, or an assumption of, the direction of m during the gradient turn. From these trial calculations, the choice of a gradient turn of the source magnet is made in the same manner as was described for a safe navigation turn above. If, due to limitations in accuracy, there is significant error in assumed change in the direction of m, it may or may not be necessary for a locator or imaging system to measure the change in direction and update the processor.

In all but unusual conditions, the procedure described above is conceptually simple, since m·B varies as mB cos θ, where θ is the angle between m and B. The direction and magnitude of m in the patient coordinate system will not change significantly in the types of navigation likely to be used. However, due to the transformations between coordinate systems the quantity cos θ will change from 1 to 0 as the source magnet is moved (in the example illustrated in FIGS. 15A and 15B) so that the transformed operating point 42 moves from a point on the axis of the source magnet axis to a point on its equatorial plane in the source magnet coordinates, that is θ goes from 0 degrees to 90 degrees. In the process, the quantity B will change in the patient, since the side field of the source magnet is less than the axial field of the source magnet, at a given distance. This may be not important, since the field strength for pulling a magnetic material into an aneurysm will be separately input by special requirements. To fulfill the needed change in the strength of B, the source magnet 38 will be translated closer to or further from the operating point 42 in the patient.

In another embodiment, such as the orienting and pulling of a magnet-tipped electrode against an interior heart chamber wall, it may be necessary to retain an orienting magnetic field in a direction approximately parallel to the wall, while exerting a pulling gradient approximately towards the wall. This may occur in a manner in which the magnet tip or tip ensemble on the electrode have in their design the capability of responding directly to a transverse gradient, and not responding in that manner to a longitudinal gradient. Special tip designs are needed, such as described in U.S. patent application Ser. No. 09/311,686, filed May 13, 1999, for Magnetic Medical Device and Method of Navigating Magnetic Medical Devices with Magnetic Fields and Gradients, incorporated herein by reference. In such a case, information specific to the design of the particular magnetic tip 46 will have been entered in the processor 22 at the start of the procedure. The magnetic tip 46 will be navigated to the procedure location, such as a chamber of the heart, in a manner similar to that of a simple magnet tip. When the tip has been navigated to the desired point, the source magnet can be turned so as to progressively move the gradient from longitudinal to transverse, while holding the tip against the wall, as described above. While changing the gradient direction, the magnet tip 46 is held towards the wall by applying a torque with the magnetic field direction. The magnet tip 46 is held against the wall in this manner while the gradient is being applied to pull the magnet tip toward the wall. In essence, there is a continuous transition from a guidance-dominant situation to a pull-dominant situation.

One embodiment of system for carrying out navigations in accordance with the methods of this invention is indicated generally as 200 in FIGS. 7A and 7B. The system 200 comprises a patient bed 202 for supporting the patient, an imaging system 204 for providing images of the operating region within a patient on the patient bed 202, and a magnet system 206 for projecting magnetic fields and gradients into the operating region in a patient on the patient bed 202.

The imaging system 204 comprises a C-arm apparatus 208, mounting two pairs of imaging beam source 210 and imaging plates 212, which are preferably mutually perpendicular. The C-arm apparatus includes a generally L-shaped support 214 that is mounted on base 216 for pivoting about a generally vertical axis, an intermediate support 218 that is mounted on L-shaped support for rotation about a generally horizontal axis; and a C-shaped bracket 220 that is mounted on the intermediate support for rotation about the central axis of the C-shaped bracket.

The magnet system 206 comprises a source magnet 222 and an articulation device 224 for translating and rotating the source magnet 222. The source magnet is preferably a superconducting electromagnet, with associated cryocooler 226. The housing conventionally used is omitted to show the configuration of the magnet. The articulation device 224 provides movement of the magnet 222 with three degrees of freedom (two rotations and one translations). The articulation device 224 comprises a base 228 that is mounted on tracks 230 for translation toward and away from the patient bed, thereby allowing translation of the magnet 222 toward and away from the operating region within a patient on the patient bed 202 (i.e. along the z axis as described above). The articulation device 224 includes a C-shaped arm 232, that is mounted on the base 228 for rotation about a first generally horizontal axis, which allows a first rotation of the magnet 222. The magnet 222 is also mounted to the C-shaped arm 232 for rotation about a second axis generally perpendicular to the first generally horizontal axis, which allows a second rotation of the magnet.

The movement of the base 228 on the tracks 230, rotation of the C-shaped arm 232 relative to the base, and the rotation of the magnet 222 relative to the C-shaped arm provides magnet motion with three degrees of freedom, and each of these movements can be controlled by a microprocessor as described herein, to project a desired magnetic field and or gradient into an operating region within a patient on the patient support.

FIG. 7B shows the system 200 with a surface 234 of constant field strength projected around the magnet 222. In navigations using this constant field strength, it is apparent there is at least one significant exclusion zone surrounding the location where the cryocooler 226 projects through the surface 234. Rotations and translations that would attempt to bring this exclusion zone to the operating region within the patient must be prohibited, because the cryocooler would strike the patients. Other rotations and translations that would bring this exclusion zone into contact with other structures in the operating room, for example with the imaging system 204 or the articulation device 224, or interfere with the imaging beams from the imaging system 204, must also be prohibited as described below.

Another embodiment of system for carrying out navigations in accordance with the methods of this invention is indicated generally as 300 in FIGS. 7C through 7I. The system 300 comprises a patient bed 302 for supporting the patient, an imaging system 304 for providing images of the operating region within a patient on the patient bed 302 patient, and a magnet system 306 for projecting magnetic fields and gradients into the operating region in a patient on the patient bed 302.

The imaging system 304 comprises a C-arm apparatus 308, mounting two pairs of imaging beam source 310 and imaging plates 312, which are preferably mutually perpendicular. The C-arm apparatus includes a generally L-shaped support 314 that is mounted on base 316 for pivoting about a generally vertical axis, an intermediate support 318 that is mounted on L-shaped support for rotation about a generally horizontal axis; and a C-shaped bracket 320 that is mounted on the intermediate support for rotation about the central axis of the C-shaped bracket.

The magnet system 306 comprises a source magnet 322 and an articulation device 324 for translating and rotating the source magnet 322. The source magnet 322 is preferably a superconducting electromagnet, with associated cryocooler 326, the magnet is surrounded by a housing 328. The articulation device 324 provides movement of the magnet 322 with five degrees of freedom (three rotations and two translations). The articulation device 324 comprises a base 330 that is mounted on tracks 332 for translation toward and away from the patient bed 302, thereby allowing translation of the magnet 322 toward and away from the operating region within a patient on the patient bed 302 (i.e., along the z axis as described above). A turntable 334 is mounted on the base 330 for rotation about a generally horizontal axis. The turntable 334 has a track 336 extending diametrically across it for slidably mounting a support arm 338, so that the support arm can translate within the track. The magnet is mounted on the end of the support arm. More specifically a C-shaped arm 340 is mounted on the end of the support arm 338, for rotation about a first axis. The magnet 322 is mounted to the C-shaped arm 340 for rotation about a second axis generally perpendicular to the first axis.

The movement of the base 330 on the tracks 332, rotation of the turntable 334 relative to the base, the translation of the support arm 338 relative to the turntable 334, the rotation of the C-shaped arm 340 relative to the support arm, and the rotation of the magnet relative to the C-shaped arm provides magnet motion with five degrees of freedom, and each of these movements can be controlled by a microprocessor as described herein, to project a desired magnetic field and or gradient into an operating region within a patient on the patient support.

Figure 7E:
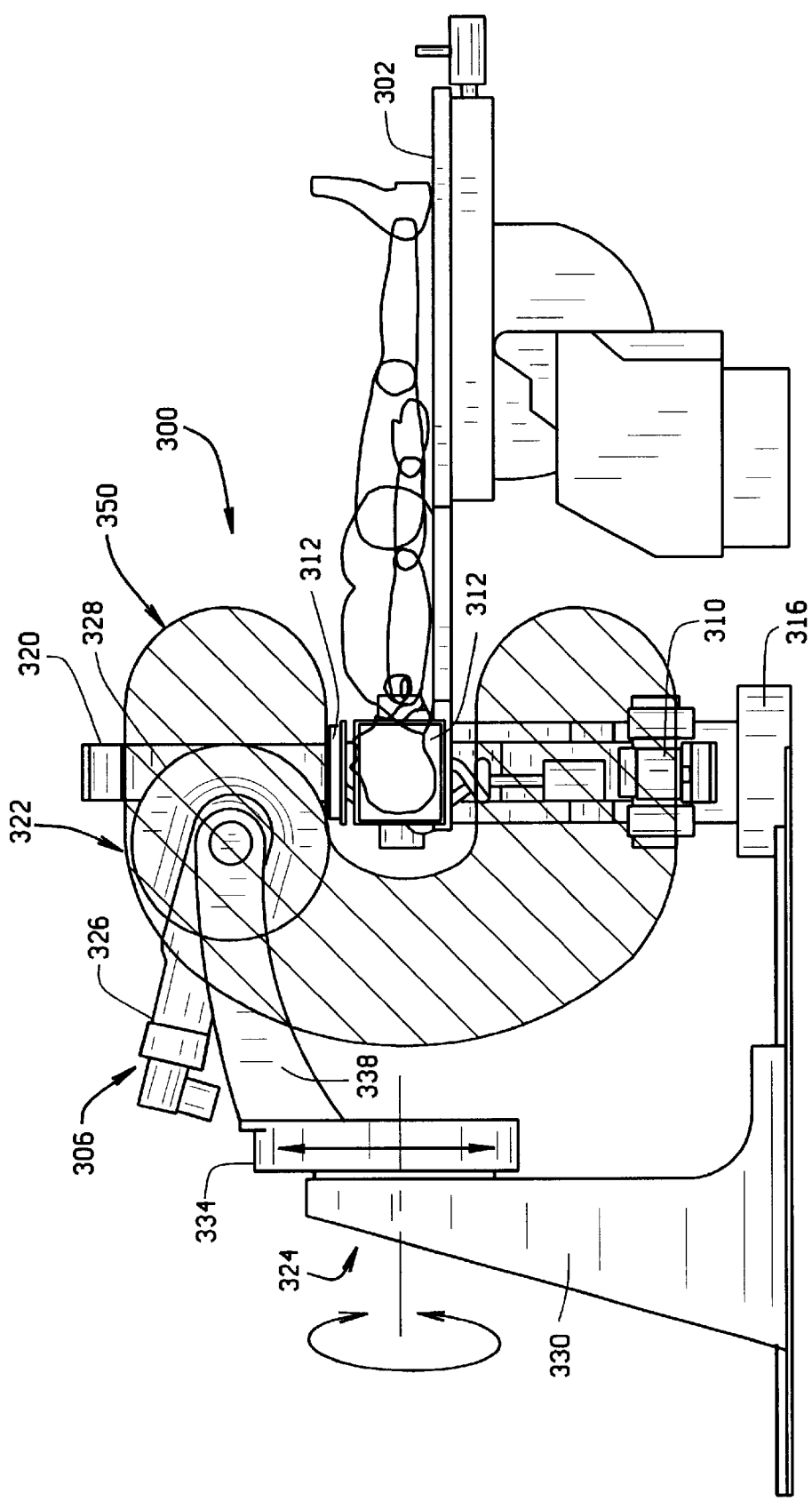
FIG. 7E is a side elevation view of the single magnet system shown in FIG. 7C, showing a work envelope in which the single magnet can move above a patient, around the end of the patient, and below the patient.
Figure 7F:
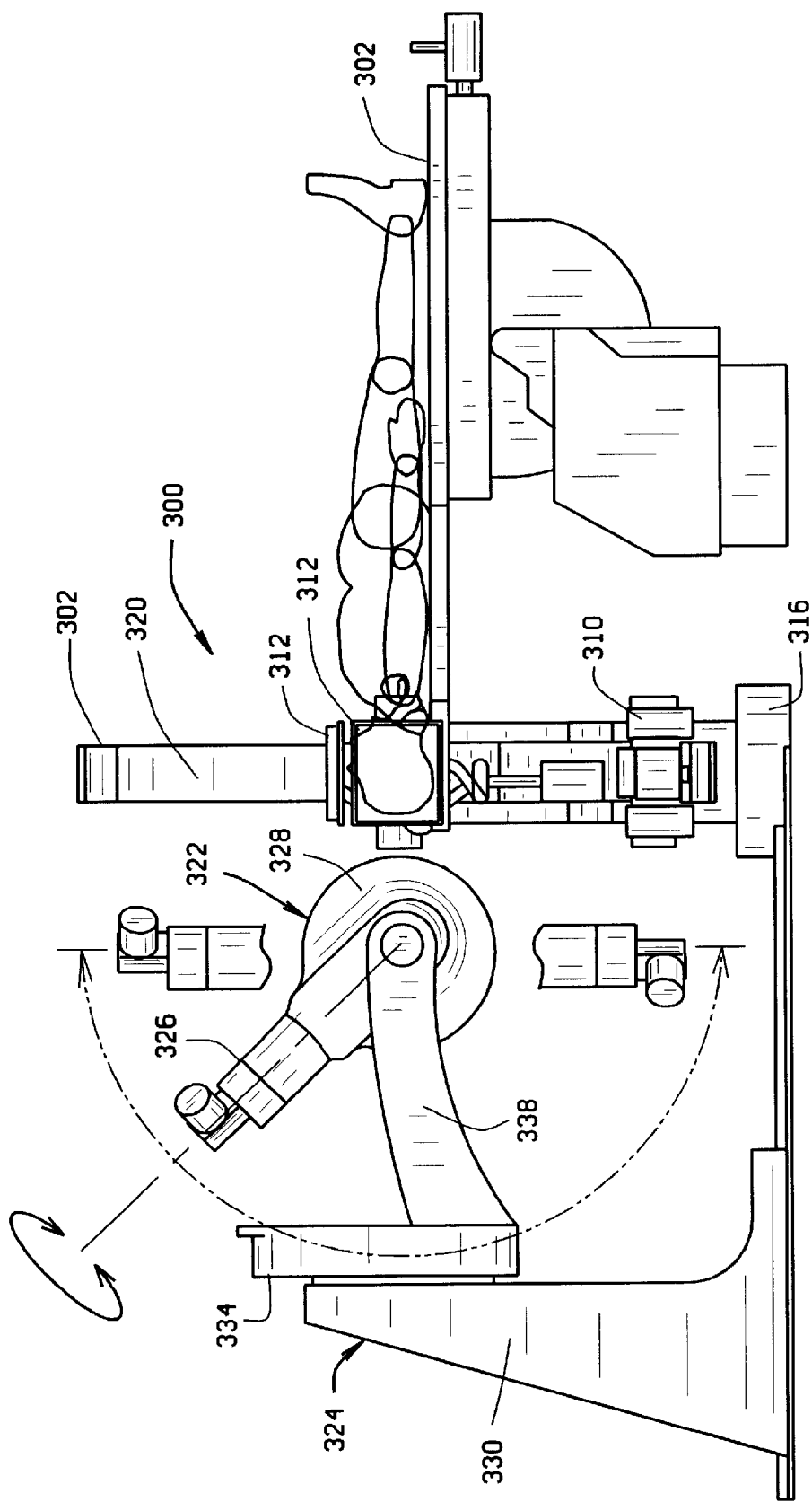
FIG. 7F is a side elevation view of the single magnet system showing the magnet behind the patient's head and showing clearance required for the rotation of the single magnet.

FIG. 7E shows the system 300 with a work envelope 350 surrounding the patient, defining the volume in which the articulation device 324 can translate the magnet 322. FIG. 7F shows the system 300 illustrating the range of motion of magnet, illustrating a maximum 360 degree rotation of the magnet 322 about the C-shaped 340 (not shown in FIG. 7F), and a maximum 180 degree rotation of the C-shaped arm 340, relative to the support arm 338.

Figure 7G:
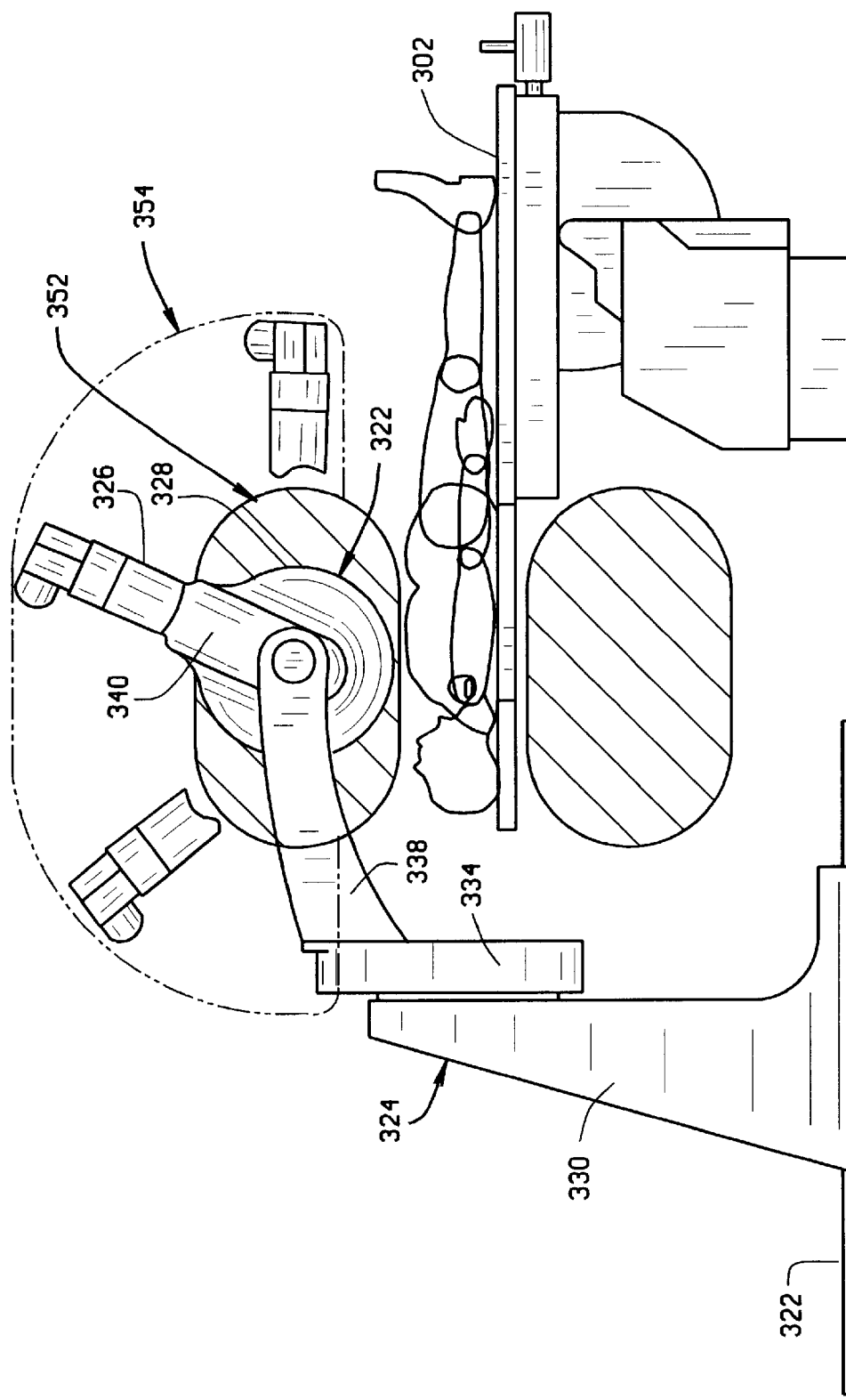
FIG. 7G is a side elevation view of the single magnet system showing the magnet work envelope in which the single magnet can translate and rotates, in an annulus around a patient's body, and the sweep volume required to accommodate rotations of the single magnet in the magnet work envelope.
Figure 7H:
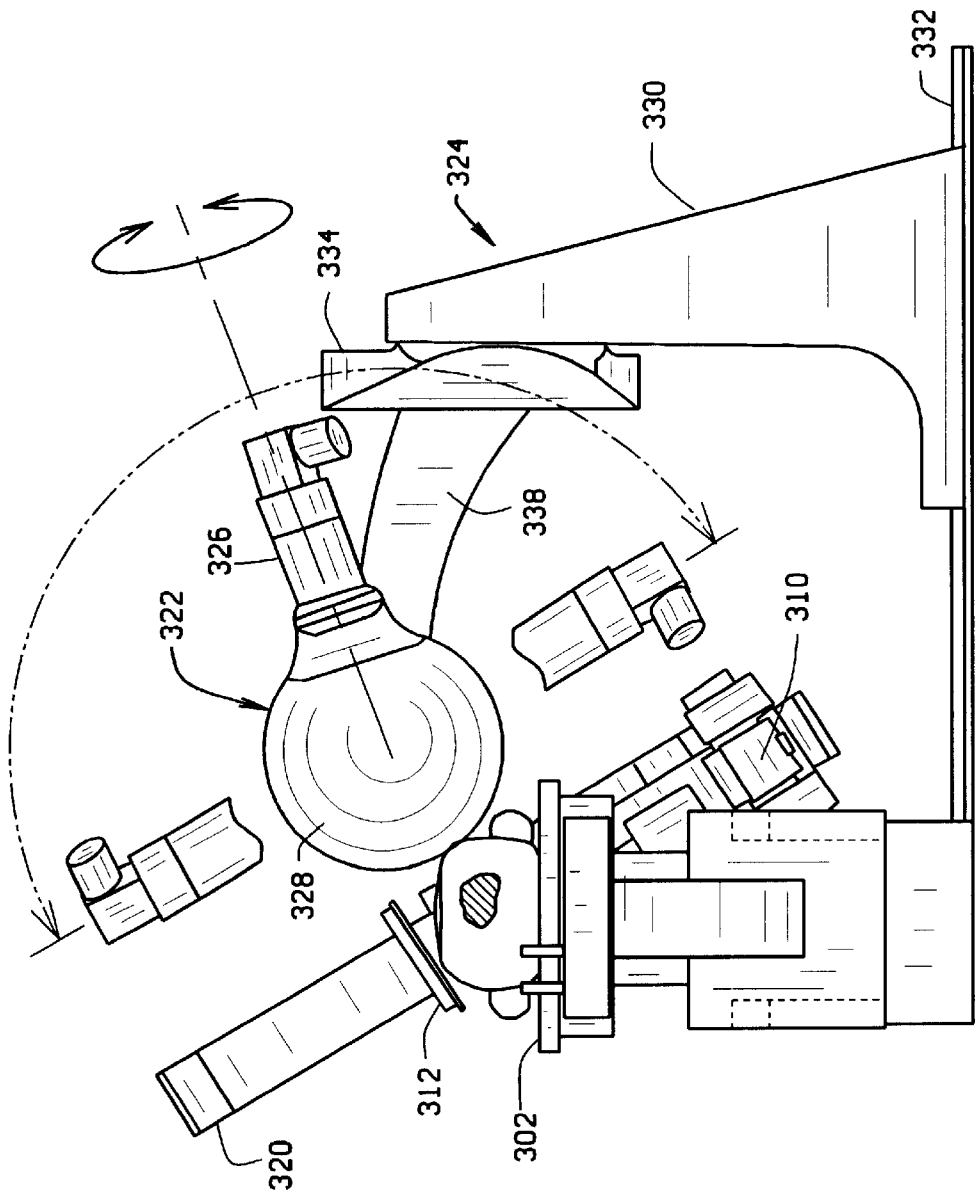
FIG. 7H is a side elevation view of the single magnet system showing the source magnet rotated in cardiac to provide better access for the single magnet to the patient.

FIG. 7G shows the system 300 illustrating a magnet work envelope 352 within which the magnet 322 can be translated and the sweep volume 354 that must be clear to accommodate the cryocooler 324 as the C-shaped support arm 340 and the magnet 322 rotate for a given translational position of the magnet in the work envelope 352. FIG. 7H shows the system 300 illustrating a rotation of the magnet 322 to provide access for the magnet to project the desired magnet field and/or gradient in the operating region in a patient on the patient bed 302. FIG. 7I shows the system 300 and illustrates the clearance between the work envelope around in the patient in which the magnet 322 moves, and the support for the imaging system.

In navigations using the system 300, it is apparent there are significant limitations on the positions and orientations of the magnet to avoid contact with the patient, other equipment in the operating room, and imaging beams from the imaging apparatus. These limitations can be addressed using exclusion zones, as described in more detail below.

Use of Exclusion Zones

For some of the procedures for which the magnetic navigation method of the present invention may be employed, there will be congestion in the region surrounding the patient, making it difficult to articulate a source magnet in ways desired to provide guiding fields in all needed directions and at required magnitudes. Primarily, the magnet and its accoutrements cannot be translated or rotated in such a way that they impinge upon the patient or any of surrounding medical equipment, including for example the patient bed and the imaging equipment, or interfere with the imaging beams. The processor 22 can control the movement of the source magnet 38 so that the interference does not occur, and can even anticipate interferences for a planned path of a number of turns for the navigated object.

The processor 22 can determine the necessary safe and efficient steps, or component parts of a step, in a path of navigation. Each such step requires rotation and/or translation of the source magnet, and the processor calculates these by transforming the desired step, in the patient reference frame, to its geometrical counterpart in the source magnet reference frame, and calculates efficient and safe source magnet motions to accomplish the field changes in the patient reference frame, as described herein. The following steps can be implemented to avoid these interferences:

The geometric "edge" of the patient, imaging equipment, etc. on the side facing the source magnet 38, can be thought of as a somewhat complex "sheet". This sheet can be defined in the coordinates of the patient reference frame by a set of vectors from the origin of that frame to appropriate points on the "patient sheet". The number and distribution of these vectors can vary, depending on the complexity of the sheet and the desired geometrical resolution in its description. Nevertheless, they can be stored in the processor memory, for example as a look-up table, or instead as a set of equations for geometrical objects.

Similarly, a "source magnet sheet" can be described in the articulatable (moveable) magnet reference frame as a set of vectors in those coordinates. On any anticipated move of the source magnet 38, the processor 22 can test for overlap or touching of the two sheets by transforming either one to the reference frame of the other. Moreover, the processor can determine (and present on a display if desired) the closest distances if there is not yet an interference.

When these "tests"0 are applied to an articulation which is used to place a vector magnetic field in the patient, there are a number of ways of accomplishing the desired directional change of the magnetic field, some more geometrically efficient than others. The injection of interference avoidance as a constraint on possible articulations must then be combined with the vector field properties of the magnet in testing for alternate articulation in any given desired move.

The specific steps involved in this combination will depend on the number and types of degrees of freedom of the articulation mechanism 36. Specifically: (A) A 3-degree of freedom system will have no available redundancy for a single move. In such cases multiple moves must be planned ahead for interferences, if necessary using tolerances in the provided field direction. (B) Systems with 4 or more degrees of freedom can have remaining choice(s) for each specific move. Among other things, these choices offer different angles for the "magnet sheet" to approach the "patient sheet". They can offer alternate articulations for a given planned path without using field direction tolerance.

The way this can be put into the navigation trial solutions is shown in FIG. 10, in which "trial" moves shown as $P_i$, and $P_n$, etc. are rotations and/or translations of the source magnet 38 which will be able to make a given direction change of the field B in the patient (given sufficient number of degrees of freedom) at the point operating point 42 where the magnet tip 46 is to be navigated, while maintaining a constant field magnitude B.

Given the patient and source magnet sheets as previously described, the processor 22 will be able to determine regions of these $P_i$ directions which are not permissible for a proposed turn, and thereby restrict the solution set. It is to be understood that each of these vectors $P_i$ corresponds to the same or nearly the same turn of B in the patient, and they differ only in the way they use the excess degrees of freedom of the articulation mechanism 36. (A result of this will be a change in the "efficiency" of the turn which can be defined as the amount of turning and translating of the source magnet to provide such a safe and correct (planar) turn of the vector B in the patient.)

What is claimed is:

1. A method of turning a medical device, having a magnetically responsive element associated with its distal end, at an operating point within an operating region inside a patient's body from an initial direction to a desired final direction, through the movement of at least one external source magnet, the method comprising:

identifying a series of intermediate directions between the initial direction and the desired final direction, each intermediate direction being substantially in the plane containing the initial direction and the desired final direction;

determining the magnetic field direction at the operating point that will cause the magnetically responsive element to align with each of series of intermediate directions and the desired final direction;

successively moving the at least one source magnet to apply the determined magnetic field directions to align the magnetic medical device with each of the series of intermediate directions and the desired final directions.

2. The method according to claim 1 wherein the step of successively moving the at least one source magnet to apply the determined magnetic field directions to align the magnetic medical device with each of the series of intermediate directions and the desired final directions is done to so that the magnetic field strength at the operating point remains substantially constant.

3. The method according to claim 1 further comprising the step of determining the required movements of the at least one source magnet before moving the at least one source magnetic, and testing the required movements by calculating the amount by which the direction of the magnet medical device would from the plane of the initial direction during the determined required movements, and identifying a different series of intermediate directions if the variation exceeds a predetermined threshold.

4. The method according to claim 1 wherein the step of moving the at least one source magnet comprises determining an orientation of the at least one source magnet to apply the determined field direction.

5. The method according to claim 4 wherein the step of determining the orientation of the at least one source magnet to apply the determined field direction employs a look-up table.

6. The method according to claim 4 wherein the step of determining the orientation of the at least one source magnet to apply the determined field direction employs an equation characterizing the magnetic field of the source magnet.

7. The method according to claim 1 wherein the movement of the magnet from one position to another position is made by taking a number of trial movements in a plurality of different directions and testing the movement.

8. The method according to claim 1 wherein the step of identifying the magnetic field direction that will cause the magnetic medical device to align with each of the intermediate directions and the desired final direction, takes into account the lag between the applied magnetic field and the actual orientation of magnetic medical device.

9. The method according to claim 8 wherein the step of identifying the magnetic field direction that will cause the magnetic medical device to align with each of the intermediate directions and the desired final direction employs an equation to determine the lag between the applied magnetic field and the actual orientation of magnetic medical device.

10. The method according to claim 8 wherein the step of identifying the magnetic field direction that will cause the magnetic medical device to align with each of the intermediate directions and the desired final direction employs a look-up table to determine the lag between the applied magnetic field and the actual orientation of magnetic medical device.

11. The method according to claim 1 wherein identifying the magnetic field direction that will orient the magnetic element to align with each of the intermediate directions and the desired final direction is determined with an appropriate over-torque.

12. The method according to claim 1 further comprising computing the amount by which the magnetic medical device deviates from the plane containing the initial direction and final direction, and identifying a new series of intermediate directions if the deviation exceeds a predetermined threshold.

13. The method according to claim 12 wherein the step of identifying a new series of intermediate directions comprises identifying intermediate directions based upon the direction in which the deviation of the magnetic medical device from the plane of the initial direction and the desired final direction exceeds a predetermined amount.

14. The method according to claim 1 wherein the desired final direction and the series of intermediate directions are identified in the patient frame of reference, and translated to the frame of reference of the at least one source magnet.

15. The method according to claim 1 wherein there is a look-up table of prohibited movements of the at least one source magnet, and the look-up table is referenced before moving the source magnets.

16. The method according to claim 1 wherein several possible movements of the at least one source magnet are determined, and the actual movement selected is selected based upon minimizing the cost function for the movement of the at least one source magnet.

* * * * *